(12) United States Patent
Zilberman et al.

(10) Patent No.: US 11,844,537 B2
(45) Date of Patent: Dec. 19, 2023

(54) GUIDING DEVICE AND METHOD OF USING THEREOF

(71) Applicant: T.A.G. Medical Products Corporation Ltd., Kibbutz Gaaton (IL)

(72) Inventors: Roy Zilberman, Qadarim (IL); Hagay Botansky, Haifa (IL); Ben Zion Spector, Tel-Mond (IL); Amir Pansky, Atlit (IL)

(73) Assignee: T.A.G. Medical Products Corporation Ltd., Kibbutz Gaaton (IL)

( * ) Notice: Subject to any disclaimer, the term of this patent is extended or adjusted under 35 U.S.C. 154(b) by 77 days.

(21) Appl. No.: 17/319,116

(22) Filed: May 13, 2021

(65) Prior Publication Data

US 2021/0259714 A1 Aug. 26, 2021

Related U.S. Application Data

(63) Continuation of application No. 16/090,820, filed as application No. PCT/IL2017/050469 on Apr. 24, 2017, now Pat. No. 11,020,132.

(60) Provisional application No. 62/326,774, filed on Apr. 24, 2016.

(51) Int. Cl.
*A61B 17/17* (2006.01)
*A61B 17/00* (2006.01)
*A61F 2/08* (2006.01)

(52) U.S. Cl.
CPC ...... *A61B 17/1764* (2013.01); *A61B 17/1714* (2013.01); *A61B 2017/00477* (2013.01); *A61F 2/0805* (2013.01)

(58) Field of Classification Search
CPC ................... A61B 17/1764; A61B 17/1714
See application file for complete search history.

(56) References Cited

U.S. PATENT DOCUMENTS

| 854,956 A | 5/1907 | Martin |
| 1,006,468 A | 10/1911 | Des Isles |
| 1,106,767 A | 8/1914 | Young |
| 1,173,882 A | 2/1916 | Smith |
| 1,204,330 A | 11/1916 | Adair |

(Continued)

FOREIGN PATENT DOCUMENTS

| CN | 1203518 | 12/1998 |
| CN | 2469895 | 1/2002 |

(Continued)

OTHER PUBLICATIONS

Examination Report dated Sep. 1, 2021 From the Servico Publico Federal, Ministerio da Economia, Institute Nacional da Propriedade Industrial do Brasil RE Application No. BR12 2020 008361 1 and Its Summary Into English. (8 Pages).

(Continued)

*Primary Examiner* — Sameh R Boles

(57) ABSTRACT

A bone drill guiding device including a drill entry part comprising a cannula having a distal end portion and sized to receive a bone drill, a drill exit part comprising a fixation tip portion and a coupling that rigidly couples the drill entry part and the drill exit part so that longitudinal axes of the cannula distal portion and the fixation tip portion are arranged on a single mutual axis. In some embodiments, the coupling is a linear sliding coupling that parallels the single mutual axis.

20 Claims, 21 Drawing Sheets

(56) References Cited

U.S. PATENT DOCUMENTS

| | | | |
|---|---|---|---|
| 1,237,142 A | 8/1917 | Aase | |
| 1,958,399 A | 5/1934 | Stephens | |
| 3,195,378 A | 7/1965 | Cogsdill | |
| 3,540,324 A | 11/1970 | Johansson | |
| 3,690,357 A | 9/1972 | Lugo | |
| 3,702,611 A | 11/1972 | Fishbein | |
| 3,945,076 A | 3/1976 | Sung | |
| 4,411,324 A | 10/1983 | Liebig | |
| 4,475,852 A | 10/1984 | Koppelmann | |
| 4,541,423 A | 9/1985 | Barber | |
| 4,635,737 A | 1/1987 | Miyanaga | |
| 4,710,070 A | 12/1987 | Alsen et al. | |
| 4,738,255 A | 4/1988 | Goble et al. | |
| 4,883,048 A | 11/1989 | Purnell et al. | |
| 4,920,958 A | 5/1990 | Walt et al. | |
| 4,992,010 A | 2/1991 | Fischer | |
| 4,998,981 A | 3/1991 | Miyanaga | |
| 5,112,337 A | 5/1992 | Paulos et al. | |
| 5,330,468 A * | 7/1994 | Burkhart | A61B 17/1778 606/96 |
| 5,445,639 A | 8/1995 | Kuslich et al. | |
| 5,507,606 A | 4/1996 | Steiner | |
| 5,514,136 A | 5/1996 | Richelsoph | |
| 5,591,170 A | 1/1997 | Spievack et al. | |
| 5,643,273 A | 7/1997 | Clark | |
| 5,645,589 A | 7/1997 | Li | |
| 5,681,320 A | 10/1997 | McGuire | |
| 5,797,709 A | 8/1998 | Payne | |
| 5,817,095 A | 10/1998 | Smith | |
| 5,839,860 A | 11/1998 | Steiner | |
| 6,015,411 A | 1/2000 | Ohkoshi et al. | |
| 6,120,511 A | 9/2000 | Chan | |
| 6,162,227 A | 12/2000 | Eckhardt et al. | |
| 6,210,415 B1 | 4/2001 | Bester | |
| 6,358,251 B1 | 3/2002 | Mirza | |
| 6,383,188 B2 | 5/2002 | Kuslich et al. | |
| 6,679,886 B2 | 1/2004 | Weikel et al. | |
| 6,746,451 B2 | 6/2004 | Middleton et al. | |
| 6,780,175 B1 | 8/2004 | Sachdeva et al. | |
| 6,923,813 B2 | 8/2005 | Phillips et al. | |
| 7,097,648 B1 | 8/2006 | Globerman et al. | |
| 7,172,374 B2 | 2/2007 | Burr et al. | |
| 7,179,024 B2 | 2/2007 | Greenhalgh | |
| 7,485,119 B2 | 2/2009 | Thelen et al. | |
| 7,637,910 B2 | 12/2009 | Schmieding et al. | |
| 7,682,378 B2 | 3/2010 | Truckai et al. | |
| 7,914,545 B2 | 3/2011 | Ek | |
| 7,927,332 B2 | 4/2011 | Huebner et al. | |
| 7,938,835 B2 | 5/2011 | Boucher et al. | |
| RE42,757 E | 9/2011 | Kuslich et al. | |
| 8,038,678 B2 | 10/2011 | Schmieding et al. | |
| 8,038,679 B2 | 10/2011 | Wieland | |
| 8,048,079 B2 | 11/2011 | Iannarone | |
| 8,388,621 B2 | 3/2013 | Bourque et al. | |
| 9,198,676 B2 | 12/2015 | Pilgeram et al. | |
| 9,295,479 B2 | 3/2016 | Hibri et al. | |
| 9,381,021 B2 | 7/2016 | Wagner et al. | |
| 9,795,395 B2 | 10/2017 | Lizardi et al. | |
| 9,848,890 B2 | 12/2017 | Yoon et al. | |
| 9,918,722 B2 | 3/2018 | Tally et al. | |
| 9,950,445 B2 | 4/2018 | Miyanaga | |
| 10,405,872 B2 | 9/2019 | Victor et al. | |
| 11,517,329 B2 | 12/2022 | Koogle, Jr. et al. | |
| 2002/0165550 A1 | 11/2002 | Frey et al. | |
| 2002/0183758 A1 | 12/2002 | Middleton et al. | |
| 2002/0193799 A1 | 12/2002 | Chappuis et al. | |
| 2004/0126196 A1 | 7/2004 | Burr et al. | |
| 2004/0208717 A1 | 10/2004 | Greenhalgh | |
| 2004/0254585 A1 | 12/2004 | Whittaker et al. | |
| 2005/0113836 A1 | 5/2005 | Lozier et al. | |
| 2005/0131345 A1 | 6/2005 | Miller | |
| 2005/0240193 A1 | 10/2005 | Layne et al. | |
| 2006/0025774 A1 | 2/2006 | Fishbein et al. | |
| 2006/0149268 A1 | 7/2006 | Truckai et al. | |
| 2006/0195112 A1 | 8/2006 | Ek | |
| 2006/0241629 A1 | 10/2006 | Krebs et al. |
| 2006/0264957 A1 | 11/2006 | Cragg et al. |
| 2007/0123889 A1 | 5/2007 | Malandain et al. |
| 2007/0276392 A1 | 11/2007 | Beyar et al. |
| 2007/0282345 A1 | 12/2007 | Yedlicka et al. |
| 2008/0103506 A1 | 5/2008 | Volpi et al. |
| 2008/0114364 A1 | 5/2008 | Goldin et al. |
| 2008/0140078 A1 | 6/2008 | Nelson et al. |
| 2008/0154271 A1 | 6/2008 | Berberich et al. |
| 2008/0183174 A1 | 7/2008 | Sikora et al. |
| 2009/0018468 A1 | 1/2009 | Janssens |
| 2009/0171359 A1 | 7/2009 | Sterrett |
| 2009/0254092 A1 | 10/2009 | Albiol |
| 2010/0168747 A1 | 7/2010 | Lynch et al. |
| 2010/0241124 A1 | 9/2010 | Housman et al. |
| 2010/0249785 A1 | 9/2010 | Betts |
| 2010/0268234 A1 | 10/2010 | Aho et al. |
| 2011/0034910 A1 | 2/2011 | Ross et al. |
| 2011/0087257 A1 | 4/2011 | To et al. |
| 2011/0098709 A1 | 4/2011 | Malandain et al. |
| 2011/0130760 A1 | 6/2011 | Anderson et al. |
| 2011/0164937 A1 | 7/2011 | Byrne et al. |
| 2011/0166575 A1 | 7/2011 | Assell et al. |
| 2011/0166581 A1 | 7/2011 | Van Der Merwe et al. |
| 2011/0190832 A1 | 8/2011 | Taylor et al. |
| 2011/0251616 A1 | 10/2011 | Osman et al. |
| 2012/0022568 A1 | 1/2012 | Koblish et al. |
| 2012/0059382 A1 | 3/2012 | Paulos |
| 2012/0209274 A1 | 8/2012 | Belaney et al. |
| 2012/0239072 A1 | 9/2012 | Rodriguez |
| 2012/0245585 A1 | 9/2012 | Kaiser et al. |
| 2013/0030442 A1 | 1/2013 | Pilgeram et al. |
| 2013/0150859 A1 | 6/2013 | Kehres et al. |
| 2013/0165935 A1 | 6/2013 | Griffiths et al. |
| 2014/0039552 A1 | 2/2014 | Pilgeram |
| 2014/0194880 A1 | 7/2014 | Schmieding et al. |
| 2014/0257297 A1 | 9/2014 | Koogle, Jr. et al. |
| 2014/0276844 A1 | 9/2014 | Bourque et al. |
| 2014/0316413 A1 | 10/2014 | Burger et al. |
| 2014/0324052 A1 | 10/2014 | Garrison et al. |
| 2015/0073417 A1 | 3/2015 | Norton et al. |
| 2015/0150570 A1 | 6/2015 | Okuno et al. |
| 2015/0265287 A1 | 9/2015 | Berberich |
| 2016/0038157 A1 | 2/2016 | Mirochinik et al. |
| 2016/0199145 A1 | 7/2016 | Haidukewych et al. |
| 2017/0128086 A1 | 5/2017 | Slobitker et al. |
| 2017/0224359 A1 | 8/2017 | Mirochinik et al. |
| 2017/0245869 A1 | 8/2017 | Mirochinik et al. |
| 2018/0360467 A1 | 12/2018 | Slobitker et al. |
| 2019/0059910 A1 | 2/2019 | Adams et al. |
| 2019/0167281 A1 | 6/2019 | Zilberman et al. |
| 2019/0388102 A1 | 12/2019 | Slobitker et al. |
| 2020/0163684 A1 | 5/2020 | Mirochinik et al. |
| 2020/0246023 A1 | 8/2020 | Forsell |
| 2020/0275939 A1 | 9/2020 | Slobitker et al. |
| 2020/0405327 A1 | 12/2020 | Zilberman et al. |
| 2021/0259710 A1 | 8/2021 | Mirochinik et al. |
| 2021/0298768 A1 | 9/2021 | Biton et al. |
| 2022/0104834 A1 | 4/2022 | Biton et al. |
| 2022/0409216 A1 | 12/2022 | Slobitker et al. |

FOREIGN PATENT DOCUMENTS

| | | |
|---|---|---|
| CN | 1925798 | 3/2007 |
| CN | 201394046 | 2/2010 |
| CN | 101677823 | 3/2010 |
| CN | 101795629 | 8/2010 |
| CN | 201617897 | 11/2010 |
| EP | 1535579 | 6/2005 |
| EP | 1785103 | 5/2007 |
| ES | 2351563 | 2/2011 |
| JP | H02-184409 | 7/1990 |
| JP | 11-514905 | 12/1999 |
| JP | 2003-531676 | 10/2003 |
| JP | 2006-523542 | 10/2006 |
| JP | 2008-521511 | 6/2008 |
| JP | 2009-533159 | 9/2009 |
| JP | 2011-529365 | 12/2011 |
| JP | S48-62067 | 1/2012 |

(56) References Cited

FOREIGN PATENT DOCUMENTS

| JP | 2012-522604 | 9/2012 |
|---|---|---|
| JP | 2012-187384 | 10/2012 |
| JP | 2013-516275 | 5/2013 |
| JP | 2014-171864 | 9/2014 |
| JP | 2015-136589 | 7/2015 |
| JP | 2016-516524 | 6/2016 |
| JP | 2016-523542 | 8/2016 |
| JP | 2018-513735 | 5/2018 |
| WO | WO 97/16118 | 5/1997 |
| WO | WO 01/58629 | 8/2001 |
| WO | WO 01/82838 | 11/2001 |
| WO | WO 2006/060420 | 6/2006 |
| WO | WO 2007/120903 | 10/2007 |
| WO | WO 2010/013027 | 2/2010 |
| WO | WO 2010/065047 | 6/2010 |
| WO | WO 2010/111246 | 9/2010 |
| WO | WO 2010/115134 | 10/2010 |
| WO | WO 2013/192080 | 12/2013 |
| WO | WO 2014/089198 | 6/2014 |
| WO | WO 2014/174521 | 10/2014 |
| WO | WO 2016/063279 | 4/2016 |
| WO | WO 2016/162869 | 10/2016 |
| WO | WO 2017/137998 | 8/2017 |
| WO | WO 2017/187436 | 11/2017 |
| WO | WO 2018/051356 | 3/2018 |
| WO | WO 2020/026252 | 2/2020 |

OTHER PUBLICATIONS

Notice of Allowance with Interview Summary dated May 4, 2022 From the US Patent and Trademark Office Re. U.S. Appl. No. 16/877,551. (80 Pages).
English Translation Dated May 16, 2022 of Examination Report dated Apr. 20, 2022 From the Servico Publico Federal, Ministerio da Economia, Instituto Nacional da Propriedade Industrial do Brasil Re Application No. BR11 2017 008135 0 . (3 Pages).
Examination Report dated Apr. 20, 2022 From the Servico Publico Federal, Ministerio da Economia, Institute Nacional da Propriedade Industrial do Brasil Re Application No. BR11 2017 008135 0 and Its Summary Into English. (8 Pages).
Relatorio de Busca e Parecer [Search Report and Opinion] dated Mar. 24, 2021 From the Servico Publico Federal, Ministerio da Economia, Institute Nacional da Propriedade Industrial do Brasil, INPI Re. Application No. BR122020008361-1 and Its Translation Into English. (8 Pages).
Official Action dated Jul. 19, 2022 from US Patent and Trademark Office Re. U.S. Appl. No. 16/561,089. (95 pages).
Restriction Official Action dated Sep. 20, 2022 from US Patent and Trademark Office Re. U.S. Appl. No. 17/016,458. (7 pages).
Final Official Action dated Mar. 11, 2022 together with Interview Summay dated Feb. 23, 2022 from US Patent and Trademark Office Re. U.S. Appl. No. 17/552,393. (8 pages).
Final Official Action together with Interview Summary dated Oct. 13, 2022 from the US Patent and Trademark Office Re. U.S. Appl. No. 17/552,393. (18 pages).
Communication Pursuant to Article 94(3) EPC dated Mar. 16, 2022 From the European Patent Office Re. Application No. 15804626.8. (5 Pages).
Supplementary European Search Report and the European Search Opinion dated Mar. 2, 2022 From the European Patent Office Re. Application No. 19845184.1.(10 Pages).
Advisory Action Before the Filing of An Appeal Brief dated Apr. 1, 2019 From the US Patent and Trademark Office Re. U.S. Appl. No. 15/318,677. (8 pages).
Advisory Action Before the Filing of An Appeal Brief dated Feb. 28, 2018 From the US Patent and Trademark Office Re. U.S. Appl. No. 15/498,731. (3 pages).
Applicant-Initiated Interview Summary dated Jul. 18, 2018 From the US Patent and Trademark Office Re. U.S. Appl. No. 15/498,731. (4 pages).
Applicant-Initiated Interview Summary dated Feb. 26, 2019 From the US Patent and Trademark Office Re. U.S. Appl. No. 15/318,677. (3 pages).
Communication Pursuant to Article 94(3) EPC dated Mar. 1, 2018 From the European Patent Office Re. Application No. 15804626.8. (3 Pages).
Communication Pursuant to Article 94(3) EPC dated Jun. 8, 2018 From the European Patent Office Re. Application No. 17205443.9. (5 Pages).
Communication Pursuant to Article 94(3) EPC dated Mar. 16, 2021 From the European Patent Office Re. Application No. 17205443.9. (6 Pages).
Communication Relating to the Results of the Partial International Search dated May 19, 2016 From the International Searching Authority Re. Application No. PCT/IL2015/051033.
European Search Report and the European Search Opinion dated Mar. 2, 2021 From the European Patent Office Re. Application No. 20209453.8. (5 Pages).
European Search Report dated Apr. 30, 2018 From the European Patent Office Re. Application No. 17205443.9. (5 Pages).
Examination Report dated Jan. 15, 2020 From the Servico Publico Federal, Ministcrio da Economia, Institute Nacional da Propricdadc Industrial do Brasil Rc. Application No. BR112015026975-3 and Its Summary in English. (4 Pages).
Examination Report Under Sections 12 & 13 of the Patents Act, 1970 and the Patents Rules, 2003 dated Mar. 5, 2021 From the Government of India, Intellectual Property India, Patents, Designs, Trade Marks, Geographical Indications, The Patent Office Re. Application No. 201727016824. (7 Pages).
Examination Report Under Sections 12 & 13 of the Patents Act, 1970 and the Patents Rules, 2003 dated Sep. 28, 2020 From the Government of India, Intellectual Property Indis, Patents, Designs, Trade Marks, Geographical Indications, The Patent Office Re. Application No. 2954/MUMNP/2015. (7 Pages).
Final Office Action dated May 11, 2021 From the Japan Patent Office Re. Application No. 2018-241087 and Its Translation Into English. (4 Pages).
International Preliminary Report on Patentability dated May 4, 2017 From the International Bureau of WIPO Re. Application No. PCT/IL2015/051033. (11 Pages).
International Preliminary Report on Patentability dated Nov. 5, 2015 From the International Bureau of WIPO Re. Application No. PCT/IL2014/050381.
International Preliminary Report on Patentability dated Feb. 11, 2021 From the International Bureau of WIPO Re. Application No. PCT/IL2019/050876. (11 Pages).
International Preliminary Report on Patentability dated Oct. 19, 2017 From the International Bureau of WIPO Re. Application No. PCT/IL2016/050370. (12 Pages).
International Preliminary Report on Patentability dated Aug. 23, 2018 From the International Bureau of WIPO Re. Application No. PCT/IL2017/050170. (16 Pages).
International Search Report and the Written Opinion dated Aug. 4, 2016 From the International Searching Authority Re. Application No. PCT/IL2015/051033.
International Search Report and the Written Opinion dated Oct. 7, 2016 From the International Searching Authority Re. Application No. PCT/IL2016/050370.
International Search Report and the Written Opinion dated Sep. 10, 2014 From the International Searching Authority Re. Application No. PCT/IL2014/050381.
International Search Report and the Written Opinion dated Aug. 11, 2017 From the International Searching Authority Re. Application No. PCT/IL2017/050170. (24 Pages).
International Search Report and the Written Opinion dated Jan. 22, 2020 From the International Searching Authority Re. Application No. PCT/IL2019/050876. (19 Pages).
International Search Report and the Written Opinion dated Aug. 29, 2017 From the International Searching Authority Re. Application No. PCT/IL2017/050469. (17 Pages).
Interview Summary dated Dec. 11, 2020 from the US Patent and Trademark Office Re. U.S. Appl. No. 16/090,820, (2 pages).

(56) References Cited

OTHER PUBLICATIONS

Invitation to Pay Additional Fees dated Aug. 1, 2016 From the International Searching Authority Re. Application No. PCT/IL2016/050370.
Invitation to Pay Additional Fees dated Nov. 13, 2019 From the International Searching Authority Re. Application No. PCT/IL2019/050876. (3 Pages).
Invitation to Pay Additional Fees dated May 17, 2017 From the International Searching Authority Re. Application No. PCT/IL2017/050170. (2 Pages).
Notice of Allowance dated Feb. 3, 2021 From the US Patent and Trademark Office Re. U.S. Appl. No. 16/090,820. (22 Pages).
Notice of Allowance dated Feb. 8, 2017 From the US Patent and Trademark Office Re. U.S. Appl. No. 14/919,921. (7 pages).
Notice of Allowance dated Jun. 11, 2019 From the US Patent and Trademark Office Re. U.S. Appl. No. 15/318,677. (3 Pages).
Notice of Allowance dated Sep. 13, 2019 From the US Patent and Trademark Office Re. U.S. Appl. No. 15/519,844. (6 pages).
Notice of Allowance dated Jan. 16, 2020 From the US Patent and Trademark Office Re. U.S. Appl. No. 16/059,098. (23 pages).
Notice of Allowance dated Feb. 18, 2021 From the US Patent and Trademark Office Re. U.S. Appl. No. 16/740,597. (44 Pages).
Notice of Allowance dated Oct. 22, 2020 From the US Patent and Trademark Office Re. U.S. Appl. No. 16/090,820. (12 Pages).
Notice of Allowance dated Oct. 26, 2018 From the US Patent and Trademark Office Re. U.S. Appl. No. 15/498,731. (9 pages).
Notice of Decision of Rejection dated Sep. 4, 2018 From the Japan Patent Office Re. Application No. 2016-509605. (4 Pages).
Notice of Reason for Rejection dated Feb. 27, 2018 From the Japan Patent Office Re. Application No. 2016-509605. (2 Pages).
Notice of Reasons for Rejection dated Dec. 1, 2020 From the Japan Patent Office Re. Application No. 2017-552067 and Its Translation Into English. (9 Pages).
Notice of Reasons for Rejection dated Jul. 7, 2020 From the Japan Patent Office Re. Application No. 2017-521086. (3 Pages).
Notice of Reasons for Rejection dated Dec. 8, 2020 From the Japan Patent Office Re. Application No. 2018-241087. (4 Pages).
Notice of Reasons for Rejection dated Dec. 10, 2019 From the Japan Patent Office Re. Application No. 2017-521086. (7 Pages).
Notice of Reasons for Rejection dated Mar. 10, 2020 From the Japan Patent Office Re. Application No. 2018-241087 and Its Translation Into English. (13 Pages.
Notice of Reasons for Rejection dated Feb. 18, 2020 From the Japan Patent Office Re. Application No. 2017-552067 and Its Translation Into English. (18 Pages).
Notice of Reasons for Rejection dated Aug. 20, 2019 From the Japan Patent Office Re. Application No. 2017-521086. (7 Pages).
Notice of Reasons for Rejection dated Jan. 21, 2020 From the Japan Patent Office Re. Application No. 2016-509605. (3 Pages).
Notification of Office Action and Search Report dated Aug. 1, 2019 From the State Intellectual Property Office of the People's Republic of China Re. Application No. 201680027825.X. (7 Pages).
Notification of Office Action and Search Report dated Jun. 1, 2020 From the State Intellectual Property Office of the People's Republic of China Re. Application No. 201810460549.7. (8 Pages).
Notification of Office Action and Search Report dated May 6, 2020 From the State Intellectual Property Office of the People's Republic of China Re. Application No. 201680027825.X. (6 Pages).
Notification of Office Action and Search Report dated Jul. 9, 2019 From the State Intellectual Property Office of the People's Republic of China Re. Application No. 201580069380.7. (5 Pages).
Notification of Office Action and Search Report dated Nov. 10, 2020 From the State Intellectual Property Office of the People's Republic of China Re. Application No. 201680027825.X. (4 Pages).
Notification of Office Action and Search Report dated Aug. 15, 2017 From the Slate Intellectual Property Office of the People's Republic of China Re. Application No. 201480035299.2. (6 Pages).
Notification of Office Action dated Dec. 4, 2018 From the State Intellectual Property Office of the People's Republic of China Re. Application No. 201580069380.7 and Its Translation Into English. (4 Pages).
Notification of Office Action dated Nov. 30, 2020 From the State Intellectual Property Office of the People's Republic of China Re. Application No. 201810460549.7. (5 Pages).
Official Action dated Nov. 2, 2016 From the US Patent and Trademark Office Re. U.S. Appl. No. 14/919,921.
Official Action dated Nov. 8, 2017 From the US Patent and Trademark Office Re. U.S. Appl. No. 15/318,677. (17 pages).
Official Action dated Dec. 13, 2017 From the US Patent and Trademark Office Re. U.S. Appl. No. 15/498,731. (12 pages).
Official Action dated Jul. 17, 2017 From the US Patent and Trademark Office Re. U.S. Appl. No. 15/498,731. (13 Pages).
Official Action dated Apr. 18, 2017 From the US Patent and Trademark Office Re. U.S. Appl. No. 15/318,677. (21 pages).
Official Action dated Jan. 23, 2019 From the US Patent and Trademark Office Re. U.S. Appl. No. 15/318,677, (16 pages).
Official Action dated May 24, 2019 From the US Patent and Trademark Office Re. U.S. Appl. No. 15/519,844. (28 pages).
Official Action dated Mar. 27, 2018 From the US Patent and Trademark Office Re. U.S. Appl. No. 15/318,677. (15 pages).
Official Action dated Aug. 29, 2018 From the US Patent and Trademark Office Re. U.S. Appl. No. 15/318,677. (17 pages).
Official Action dated Mar. 29, 2018 From the US Patent and Trademark Office Re. U.S. Appl. No. 15/498,731. (15 pages).
Restriction Official Action dated Jul. 8, 2016 From the US Patent and Trademark Office Re. U.S. Appl. No. 14/919,921.
Restriction Official Action dated Feb. 11, 2016 From the US Patent and Trademark Office Re. U.S. Appl. No. 14/919,921.
Restriction Official Action dated Jul. 2, 2020 from the US Patent and Trademark Office Re. U.S. Appl. No. 16/090,820, (7 pages).
Search Report and Explanation dated Apr. 16, 2020 From the Servico Publico Federal, Ministerio da Economia, Institute Nacional da Propriedade Industrial do Brasil Re. Application No. BR112017008135-0 and Its Summary in English. (5 Pages).
Supplementary European Search Report and the European Search Opinion dated Apr. 6, 2020 From the European Patent Office Re. Application No. 17788940.9. (5 Pages).
Supplementary European Search Report and the European Search Opinion dated Dec. 13, 2018 From the European Patent Office Re. Application No. 16776225.1. (8 Pages).
Supplementary European Search Report and the European Search Opinion dated Jan. 30, 2019 From the European Patent Office Re. Application No. 17749987.8. (6 Pages).
Translation Dated Jun. 4, 2020 of Notification of Office Action dated May 6, 2020 From the State Intellectual Property Office of the People's Republic of China Re. Application No. 201680027825.X. (4 Pages).
Translation Dated Sep. 4, 2019 of Notice of Reasons for Rejection dated Aug. 20, 2019 From the Japan Patent Office Re. Application No. 2017-521086. (7 Pages).
Translation Dated Oct. 5, 2018 of Notice of Decision of Rejection dated Sep. 4, 2018 From the Japan Patent Office Re. Application No. 2016-509605. (4 Pages).
Translation Dated Feb. 7, 2020 of Notice of Reasons for Rejection dated Jan. 21, 2020 From the Japan Patent Office Re. Application No. 2016-509605. (3 Pages).
Translation Dated Dec. 9, 2020 of Notification of Office Action dated Nov. 30, 2020 From the State Intellectual Property Office of the People's Republic of China Re. Application No. 201810460549.7. (6 Pages).
Translation Dated Jan. 9, 2020 of Notice of Reasons for Rejection dated Dec. 10, 2019 From the Japan Patent Office Re. Application No. 2017-521086. (8 Pages).
Translation Dated Jul. 14, 2019 of Notification of Office Action dated Jul. 9, 2019 From the State Intellectual Property Office of the People's Republic of China Re. Application No. 201580069380.7. (1 Page).

(56) References Cited

OTHER PUBLICATIONS

Translation Dated Jun. 22, 2020 of Notification of Office Action dated Jun. 1, 2020 Fromthe State Intellectual Property Office of the People's Republic of China Re. Application No. 201810460549.7. (4 Pages).
Translation Dated Mar. 22, 2018 of Notice of Reason for Rejection dated Feb. 27, 2018 From the Japan Patent Office Re. Application No. 2016-509605. (2 Pages).
Translation Dated Aug. 23, 2019 of Notification of Office Action dated Aug. 1, 2019 From the State Intellectual Property Office of the People's Republic of China Rc. Application No. 201680027825.X. (4 Pages).
Translation Dated Nov. 26, 2020 of Notification of Office Action dated Nov. 10, 2020 From the State Intellectual Property Office of the People's Republic of China Re. Application No. 201680027825.X. (3 Pages).
Translation Dated Dec. 30, 2020 ofNotice ofReasons for Rejection dated Dec. 8, 2020 From the Japan Patent Office Re Application No. 2018-241087. (4 Pages).
Translation of Notification of Office Action dated Aug. 15, 2017 From the State Intellectual Property Office of the People's Republic of China Re. Application No. 201480035299.2. (3 Pages).
Official Action dated Jun. 24, 2022 from US Patent and Trademark Office Re. U.S. Appl. No. 17/552,393. (138 pages).
Examination Report Under Sections 12 & 13 of the Patents Act, 1970 and the Patents Rules, 2003 dated Aug. 31, 2022 From the Government of India, Intellectual Property India, Patents, Designs, Trade Marks, Geographical Indications, The Patent Office Re. Application No. 202128040474. (6 Pages).

Communication Pursuant to Article 94(3) EPC dated Nov. 11, 2021 From the European Patent Office Re. Application No. 17205443.9. (5 Pages).
Notice of Reasons for Rejection dated Apr. 12, 2022 From the Japan Patent Office Re. Application No. 2021-503166 and Its Translation Into English. (9 Pages).
Communication Pursuant to Article 94(3) EPC dated May 17, 2021 From the European Patent Office Re. Application No. 17788940.9. (6 Pages).
Communication Pursuant to Article 94(3) EPC dated Jul. 27, 2021 From the European Patent Office Re. Application No. 15804626.8. (7 Pages).
Notice of Reason(s) for Rejection dated Aug. 3, 2021 From the Japan Patent Office Re. Application No. 2017-552067 and Its Translation Into English. (9 Pages).
Notice of Allowance dated Aug. 16, 2021 from the US Patent and Trademark Office Re. U.S. Appl. No. 17/264,895. (35 pages).
Communication Pursuant to Article 94(3) EPC dated Jan. 27, 2023 From the European Patent Office Re. Application No. 16776225.1 (7 Pages).
Final Official Action dated Jan. 27, 2023 together with Interview Summary dated Jan. 6, 2023 from the US Patent and Trademark Office Re. U.S. Appl. No. 16/561,089, (43 pages).
Notice of Allowance dated Mar. 1, 2023 from the US Patent and Trademark Office Re. U.S. Appl. No. 17/552,393. (8 pages).
Notice of Reason(s) for Rejection dated Jan. 17, 2023 From the Japan Patent Office Re. Application No. 2022-001060 and Its Translation Into English. (20 Pages).
Second Restriction Official Action dated Feb. 28, 2023 from the US Patent and Trademark Office Re. U.S. Appl. No. 17/016,458. (7 pages).

* cited by examiner

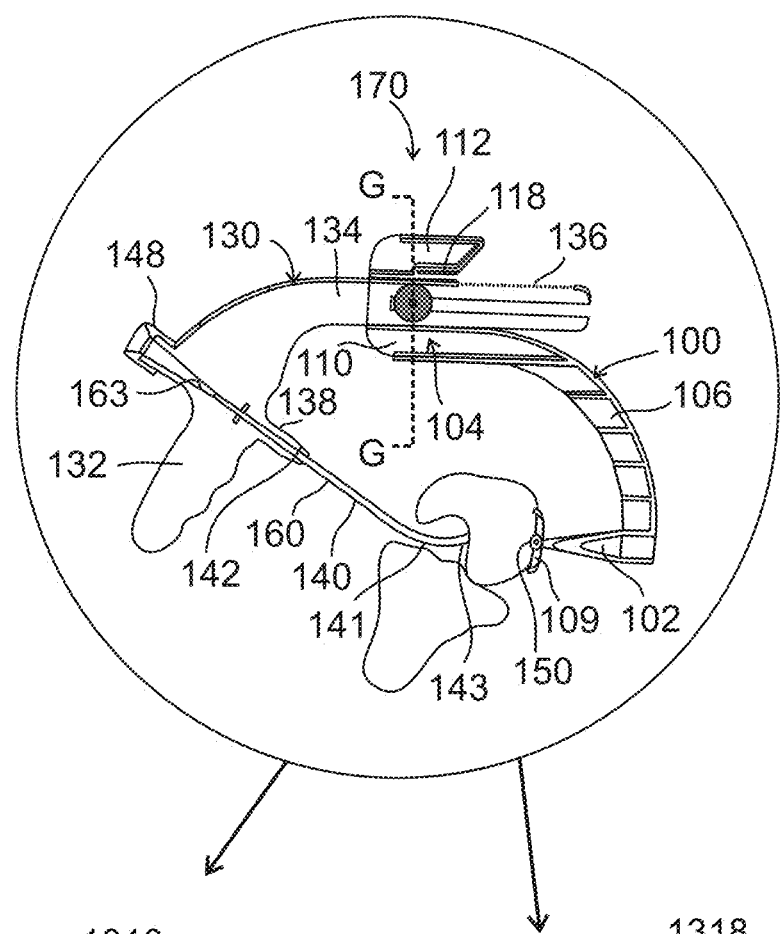
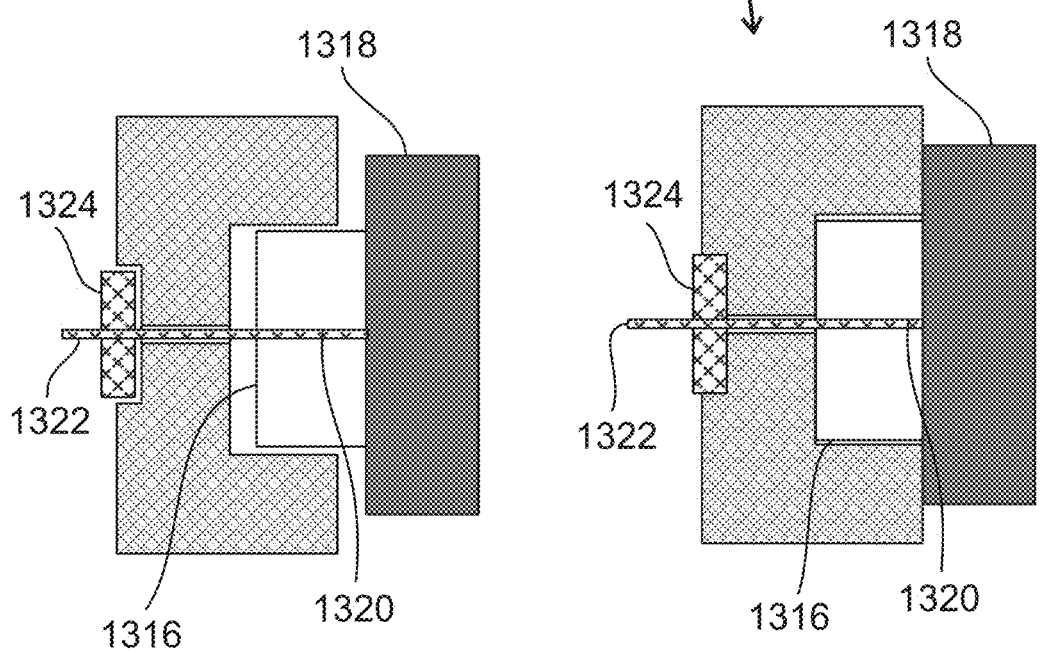
FIG. 13B
(SECTION G-G)
FIG. 13C
(SECTION G-G)

GUIDING DEVICE AND METHOD OF USING THEREOF

RELATED APPLICATIONS

This application is a Continuation of U.S. patent application Ser. No. 16/090,820 filed on Oct. 3, 2018, which is a National Phase of PCT Patent Application No. PCT/IL2017/050469 having International Filing Date of Apr. 24, 2017, which claims the benefit of priority under 35 USC § 119(e) of U.S. Provisional Patent Application No. 62/326,774 filed on Apr. 24, 2016. The contents of the above applications are all incorporated by reference as if fully set forth herein in their entirety.

FIELD OF THE INVENTION

The present invention relates to guiding devices for use in arthroscopic reconstruction procedures, particularly useful in Anterior Cruciate Ligament Reconstruction (ACL) procedures.

BACKGROUND OF THE INVENTION

It is known that during various arthroscopic procedures and particularly during Anterior Cruciate Ligament Reconstruction (ACL Reconstruction), anteromedial drilling of the femoral tunnel is required.

Different fixation techniques are employed in order to drill a bore having predetermined dimensions through the femur bone. It is important to provide accurate determination of drilling entry point and fixation of exit point during the ACL reconstruction procedure.

SUMMARY OF THE INVENTION

The present invention seeks to provide an improved guiding device for arthroscopic reconstruction procedures.

There is thus provided in accordance with an embodiment of the present invention a guiding device, including an exit point fixation assembly having a first connection portion and a tip defining exit point and adapted to be engaged with the patient's body; an entry point guiding assembly including a drilling tunnel and a second connection portion adapted to be fixedly connected to the exit point fixation assembly; and wherein at least the first connection portion and part of the drilling tunnel extend in parallel to each other.

According to an aspect of some embodiments of the present invention there is provided a bone drill guiding device, including a drill entry part sized and fitted to receive at least one curved cannula. According to some embodiments, the entry part comprises at least one curved cannula, said cannula having a distal end portion and a cannula tip and sized to receive a bone drill, a drill exit part comprising a fixation tip portion comprising a fixation tip; and a coupling that rigidly couples the drill entry part and the drill exit part so that longitudinal axes of at least the cannula distal portion and the fixation tip portion are arranged along a single mutual axis extending between said cannula tip to the fixation tip. In some embodiments, at least 50% of the curved cannula is straight.

According to some embodiments of the invention, the cannula distal portion and the fixation tip portion are arranged on opposite sides of a bone to be drilled. According to some embodiments of the invention, the fixation tip portion includes at least one marker that marks an expected drill exit point. According to some embodiments the marker has ring geometry concentric with the single mutual axis and defines a perimeter within which the drill is expected to exit. According to some embodiments a diameter of the ring depends on a bending tolerance of the drill.

According to some embodiments of the invention, the cannula includes a curved cannula. According to some embodiments, the cannula is curved in one or more directions. According to some embodiments, the cannula includes a curved portion disposed between a proximal straight portion and the straight distal end portion and the curvature of the curved portion is defined by an angle ($\Phi$) between a longitudinal axis of the straight proximal portion and a longitudinal axis of the straight distal end. According to some embodiments of the invention, the angle ($\Phi$) is between 90 and 180 degrees and according to some embodiments the angle ($\Phi$) is 45 degrees.

According to some embodiments of the invention, the coupling is adjustable and according to some embodiments includes a linear sliding coupling including a drill entrance side part linear connecting portion and a drill exit side part connecting portion. According to some embodiments the coupling includes a ratchet-type coupling. According to some embodiments the drill exit side part connecting portion includes an opening sized and fitted to slidingly receive the drill entrance side part linear connecting portion and the coupling includes one or more degrees of freedom wherein the linear connecting portion slides axially within the opening along a an axis of movement parallel to the single mutual axis. According to some embodiments, the axially sliding coupling rigidly couples said drill entry part and said drill exit part so that longitudinal axes of said cannula distal portion and said fixation tip portion are arranged on a single mutual axis extending from said cannula tip to said fixation tip parallel to the axis of movement.

According to an aspect of some embodiments of the present invention there is provided a bone drill guiding device, including a drill entry part including a cannula having a distal end portion and sized to receive a bone drill, a drill exit part including a fixation tip portion and a coupling that rigidly couples the drill entry part and the drill exit part and an indicator that indicates that longitudinal axes of said cannula distal portion and said fixation tip portion are arranged on a single mutual axis parallel to said linear coupling. According to some embodiments, the indicator indicates the spatial relationship between the longitudinal axes of the cannula distal portion and the fixation tip portion. According to some embodiments, at least a portion of at least one of the drill entrance side part and/or the drill exit side part includes the indicator. According to some embodiments, the linear connecting portion includes the indicator. According to some embodiments, the coupling includes a ratchet-type coupling and a stopper and/or a lock. According to some embodiments, the drill entrance side part includes a hollow drill insertion tunnel sized and fitted to receive the cannula and the entrance side part includes a lock that locks the cannula in the tunnel.

According to some embodiments, the cannula distal portion includes at least one spike and is configured to be placed on a surface of a bone and the fixation tip portion is configured to be placed on skin. According to some embodiments, a cannula to be used for a procedure is selected according to the curvature of said curved portion defined by an angle ($\Phi$) between a longitudinal axis of the straight proximal portion and a longitudinal axis of said straight distal end.

According to some embodiments, the hollow drill insertion tunnel extends through said drill entrance side part at an angle (β) in respect to said single mutual axis and a drill insertion tunnel selected to be used depends at least on said angle (β) and the drill insertion tunnel selected to be used depends on an angle (Φ) of a curvature of a curved portion of a cannula to be used. In some embodiments, the curved cannula is selected in accordance with the anatomy of the bone.

According to some embodiments of the invention the hollow drill insertion tunnel extends through the drill entrance side part at an angle (β) in respect to the single mutual axis, defined by a an angle (Φ) of a curvature of a curved portion of the cannula.

According to an aspect of some embodiments of the present invention there is provided a multiple angle bone drill guiding device including a drill entry part including two or more drill insertion tunnels, each sized and fitted to accommodate a cannula having a distal portion and sized to receive a bone drill, a drill exit part including a fixation tip portion; and a coupling that rigidly couples the drill entry part and the drill exit part so that longitudinal axes of at least one of the cannulas distal end and the fixation tip portion are arranged on a single mutual axis. According to some embodiments of the invention at least one of the cannulas includes a curved portion. According to some embodiments the drill insertion tunnels are arranged in the drill entry part at varying angles ($\beta_1, \beta_2 \ldots \beta_n$) in respect to the single mutual axis wherein each of the angles ($\beta_1, \beta_2 \ldots \beta_n$) is defined by a single cannula having a curved portion curved at a corresponding angle ($\Phi_1, \Phi_2 \ldots \Phi_n$).

According to some embodiments, a drill entry part comprising two or more drill insertion tunnels sized and fitted to receive a cannula.

According to some embodiments of the invention the coupling is rotatable, the device includes at least one indicator that when the device is positioned in place the indicator indicates an angle (Φ) of a curvature of a curved portion of the cannula to be used. According to some embodiments of the invention the longitudinal axes of a straight distal end of a cannula has a curved portion with a curvature angle (Φ) and the fixation tip portion are arranged on a single mutual axis.

According to an aspect of some embodiments of the present invention there is provided a method of drilling a hole in bone including positioning a drill entry part of a bone drill guiding device including a cannula against a bone at a desired drill entry point, slidingly coupling a drill exit part including a fixation tip portion to the drill entry part, sliding the drill entry and drill exit parts towards each other and positioning the fixation tip portion against skin over a location at which the drill is expected to exit the bone, rigidly locking the drill entry part and the drill exit part together; and bringing longitudinal axes of a distal portion of the cannula and the fixation tip portion to be arranged on a single mutual axis. According to an aspect of some embodiments the method further includes inserting a bone drill through the cannula and drilling a hole through the bone until the drill exits at an exit point defined by the fixation tip portion.

According to an aspect of some embodiments of the present invention there is provided a bone drill guiding device, including a drill entry part including a cannula having a distal end portion and sized to receive a bone drill, a drill exit part including a fixation tip portion and a linear sliding coupling that rigidly couples the drill entry part and the drill exit part so that longitudinal axes of the cannula distal portion and the fixation tip portion are arranged on a single mutual axis parallel to the linear coupling. According to some embodiments, the cannula includes a curved cannula and/or the cannula includes a curved portion disposed between a proximal straight portion and the straight distal end portion, the curvature of the curved portion is defined by an angle (1) between a longitudinal axis of the straight proximal portion and a longitudinal axis of the straight distal end.

According to an aspect of some embodiments of the present invention there is provided a bone drill guiding device, including a drill entry part including a cannula having a distal end portion and sized to receive a bone drill, a drill exit part comprising a fixation tip portion and a coupling that rigidly couples the drill entry part and the drill exit part and at least one indicator that indicates that longitudinal axes of the cannula distal portion and the fixation tip portion are arranged on a single mutual axis parallel to the linear coupling.

BRIEF DESCRIPTION OF THE SEVERAL VIEWS OF THE DRAWINGS

The present invention will be understood and appreciated more fully from the following detailed description, taken in conjunction with the drawings in which:

FIGS. 13A, 13B and 13C are partial sectional view simplified illustrations of a drill guiding device in accordance with some embodiments of the present invention;

DETAILED DESCRIPTION OF PREFERRED EMBODIMENTS

Figure 1A:
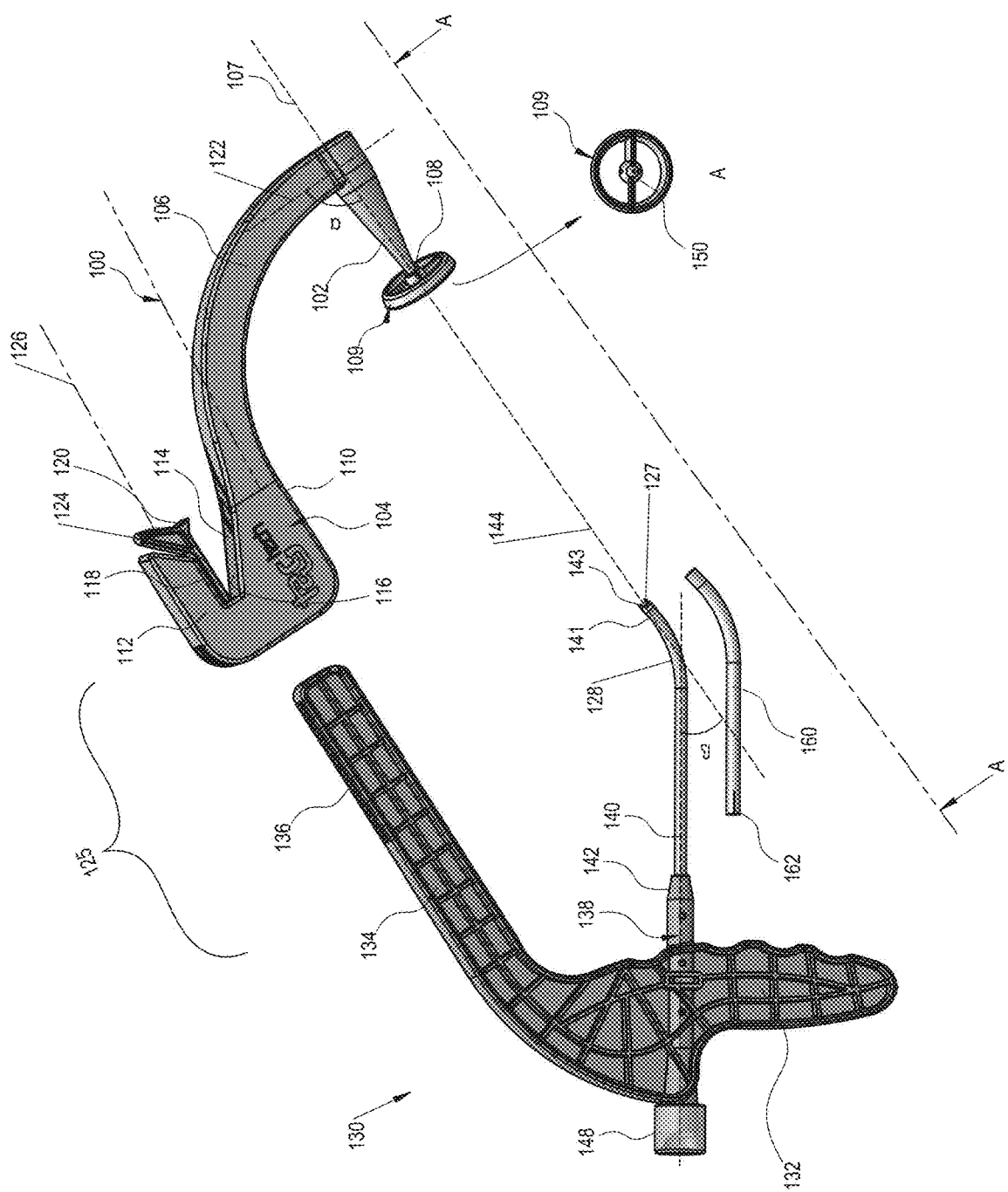
FIGS. 1A & 1B are a simplified exploded view illustration and sectional view illustration respectively of a guiding device comprised of an exit point fixation assembly and an entry point guiding assembly, section being taken along lines A-A in FIG. 1A, the guiding device constructed and operative in accordance with some embodiments of the present invention.

The present invention relates to drill guiding devices for use in arthroscopic reconstruction procedures, particularly useful in Anterior Cruciate Ligament Reconstruction (ACL) procedures.

An aspect of some embodiments of the current invention relates to a drill guiding device that defines an exit point area of a tunnel drilled in a bone. In some embodiments, the device comprises a frame comprising at least a drill entrance side part and a drill exit side part. In some embodiments, the drill guide comprises an indicator, indicating the spatial relationship between the drill entrance side part and a drill exit side part. In some embodiments, a portion of at least of one of the drill entrance side part and/or the drill exit side part comprises the indicator. In some embodiments, the indicator indicates that longitudinal axes of said cannula distal portion and said fixation tip portion are arranged on a single mutual axis parallel to said linear coupling. In some embodiments, the cannula comprises a cannula tip and the fixation tip portion comprises a fixation tip and the single mutual axis extends from said cannula tip to said fixation tip. In some embodiments, the expected exit point of the drill is located on the single mutual axis.

In some embodiments, the two parts are movably coupled. In some embodiments, when coupled, the two parts can be moved axially towards and away from each other. In some embodiments, the two parts can be locked in place at a desired distance one from the other. In some embodiments, when coupled, the movement of the two parts comprises one degree of freedom. In some embodiments, the parts are coupled via an adjustable coupling. In some embodiments, the adjustable is a sliding coupling. In some embodiments, the sliding coupling comprises a stopper. In some embodiments, the stopper is configured to rigidly and fixedly lock the coupling. In some embodiments, the sliding coupling is lockable at any position. In some embodiments, the sliding coupling is a ratchet-type coupling. In some embodiments, the ratchet-type sliding coupling comprises a stopper. In some embodiments, the ratchet-type adjustable coupling rigidly couples the drill entrance side part and the drill exit side part. In some embodiments, the frame has generally arc geometry.

In some embodiments, the drill entrance side part comprises at least a drill insertion guide. In some embodiments, the drill insertion guide comprises a drill insertion tunnel and a cannula. In some embodiments, a portion of the cannula is curved. In some embodiments, the cannula is curved in one or more directions. In some embodiments the cannula comprises a curved portion. In some embodiments, the curved portion is disposed between a proximal straight portion coupled to the drill insertion tunnel and a straight distal end of the cannula. In some embodiments, the straight distal portion extends between 5 and 20 mm, 7 and 15 mm, 10 and 12 mm, less than 5 mm or more than 20 mm distal to the distal edge of the curved portion. In some embodiments, the straight distal end comprises at least 10% of the length of the cannula. In some embodiments, the straight distal end comprises between 2% and 10% of the total length of the cannula. In some embodiments, the straight distal end comprises between 10% and 20% of the total length of the cannula. In some embodiments, the cannula comprises a straight distal end distal to the curve having a drill insertion guide tip. In some embodiments, the tip comprises at least one spike. In some embodiments, an angle (Φ) between the longitudinal axis of the straight proximal portion of the cannula and the longitudinal axis of the straight distal end distal to the curved portion defines the degree of curvature of the curved portion.

In some embodiments, the drill exit side part of the drill guide device comprises a fixation tip portion. In some embodiments, when the drill entrance side part and the drill exit side part are coupled, the distal end of the cannula and the fixation tip portion lie on opposite sides of the bone along a same longitudinal axis. In some embodiments, the drilled tunnel lies along the same longitudinal axis.

An aspect of some embodiments of the current invention relates to a drill guiding device that indicates to a surgeon drilling a tunnel in bone the exact angle of the tunnel at each point in time and predicts an exit point of the tunnel within a defined perimeter. In some embodiments, the device comprises a frame comprising at least a drill entrance side part having a curved drill guide cannula comprising a straight distal end portion and a drill exit side part. In some embodiments, the two parts are movably coupled.

In some embodiments, the coupling comprises a drill entrance side part linear connecting portion. In some embodiments, drill exit side part comprises a connecting portion. In some embodiments, when coupled to the drill entrance side part linear connecting portion the drill exit side part connecting portion is axially slidable along the drill entrance side part linear connecting portion. In some embodiments, the drill entrance side part linear connecting portion defines a first longitudinal axis and the drill guide cannula straight distal end and the fixation tip portion of the drill exit side part are arranged along a single mutual second longitudinal axis.

In some embodiments, the first longitudinal axis is parallel to the second longitudinal axis. In some embodiments, the first longitudinal axis is maintained parallel to the second longitudinal axis throughout movement of the drill exit side part connecting portion in respect to the drill entrance side part linear connecting portion.

In some embodiments, the drill entrance side part and the drill exit side part are reversibly rigidly coupled via the ratchet-type adjustable coupling. In some embodiments, the first longitudinal axis is maintained parallel to the second longitudinal axis of the drill entrance side part and the drill exit side part coupling with any movement of the drill guide in respect to the bone. In some embodiments, when coupled, the movement of the two parts comprises one degree of freedom.

In some embodiments, the drill entrance side part and the drill exit side part coupling a ratchet-type sliding coupling. In some embodiments, the ratchet-type sliding coupling comprises a stopper.

In some embodiments, the drill entrance side part comprises at least a drill insertion guide. In some embodiments, the drill insertion guide comprises a drill insertion tunnel. In some embodiments, the drill insertion tunnel is fixedly coupled to the drill insertion guide. In some embodiments, the drill insertion guide comprises a cannula fixedly coupled to the drill insertion tunnel. In some embodiments, the tunnel and the cannula are arranged axially along a same first longitudinal axis. In some embodiments, the drill exit side part of the drill guide device comprises a fixation tip portion. In some embodiments, when the drill entrance side part and the drill exit side part are coupled, the cannula and the fixation tip portion lie on opposite sides of the bone along a same first longitudinal axis. In some embodiments, the drilled tunnel lies along the same longitudinal axis.

In some embodiments, the drill exit side part comprises a fixation tip portion. In some embodiments, when the drill entrance side part and the drill exit side part are coupled, the cannula and the fixation tip portion lie on opposite sides of the bone along a same first longitudinal axis. In some embodiments, fixation tip portion comprises a marker that marks the exit point. In some embodiments, the marker is outside of the body. In some embodiments, the marker is positioned on the skin. In some embodiments, the marker has circular geometry. In some embodiments, the marker has ring geometry. In some embodiments, the ring defines a perimeter within which the exit point of the drilled tunnel may exit. In some embodiments, the diameter of the ring depends on the bending tolerance of the drill. In some embodiments, the marker functions as a securing element.

In some embodiments, the device comprises a frame comprising at least a drill entrance side part having a curved drill guide cannula comprising a straight distal end portion and a drill exit side part. In some embodiments, the two parts are movably coupled. In some embodiments, the coupling allows nonlinear (e.g., rotational) movement of the drill entrance side part in respect to the drill exit side part. In some embodiments, the drill guide device comprises an indicator that indicates that when the drill guide cannula straight distal end and the fixation tip portion of the drill exit side part are arranged along the single mutual second longitudinal axis.

An aspect of some embodiments of the invention relates to a drill stabilizing drill guiding device. In some embodiments, the device comprises a frame that immovably locks a drill guide in place. In some embodiments, the device comprises a frame comprising at least a drill entrance side part and a drill exit side part. In some embodiments, when coupled, the drill entrance side part is in direct contact with a bone to be drilled and the drill exit side part is in direct contact with skin located over the bone to be drilled. In some embodiments, the drill exit side part is positioned on an opposite side to the drill entrance side part. In some embodiments, the drill stabilizing drill guiding device has two or more points of contact with the body of a patient. In some embodiments, at least a first point of contact is located at the drill entry point. In some embodiments, at least a second point of contact is at an estimated drill exit point from the bone. In some embodiments, at least the first and second points of contact diametrically oppose each other. In some embodiments, the two parts are movably coupled. In some embodiments, when coupled, the two parts can be moved axially towards and away from each other. In some embodiments, the two parts can be locked in place at a desired distance one from the other. In some embodiments, when coupled, In some embodiments, the parts are coupled via a sliding coupling. In some embodiments, the sliding coupling comprises a stopper. In some embodiments, the stopper is configured to rigidly and fixedly lock the coupling. In some embodiments, the sliding coupling is lockable at any position. In some embodiments, the sliding coupling is a ratchet-type coupling. In some embodiments, the ratchet-type sliding coupling comprises a stopper. In some embodiments, the ratchet-type adjustable coupling rigidly couples the drill entrance side part and the drill exit side part.

An aspect of some embodiments of the current invention relates to a multiple angle drill guiding device. In some embodiments, the device comprises a frame comprising at least a drill entrance side part and a drill exit side part. In some embodiments, the two parts are movably coupled. In some embodiments, the coupling comprises a drill entrance side part linear connecting portion. In some embodiments, the connecting portion lies along a straight line. In some embodiments, drill exit side part comprises a connecting portion. In some embodiments, when coupled to the drill entrance side part linear connecting portion the drill exit side part connecting portion is axially slidable along the drill entrance side part linear connecting portion. In some embodiments, when coupled, the movement of the two parts comprises one degree of freedom.

In some embodiments, the drill entrance side part and the drill exit side part coupling a ratchet-type sliding coupling. In some embodiments, the ratchet-type sliding coupling comprises a stopper.

In some embodiments, the drill entrance side part comprises one or more slots. In some embodiments, the one or more slots are configured to fixedly accommodate one or more drill insertion guides. In some embodiments, the drill insertion guide comprises a drill insertion tunnel. In some embodiments, the drill insertion tunnel is fixedly coupled to the drill insertion guide. In some embodiments, the drill insertion guide comprises a cannula fixedly coupled to the drill insertion tunnel. The tunnel is curved. In some embodiments, the cannula comprises a proximal portion proximal to the curve rigidly coupled to the drill insertion tunnel and a distal end distal to the curve. In some embodiments, the longitudinal axis of the distal end is parallel to the longitudinal axis of the ratchet-type coupling. A guiding device (e.g., for accurate anteromedial drilling of the femoral tunnel during ACL reconstruction) is constructed and operative in accordance with an embodiment of the present invention.

The guiding device provides for fixation of drilling entry point into bone and accurate determination of drilling exit point as well as the angle of a tunnel being drilled in bone at each point in time.

Figure 1B:
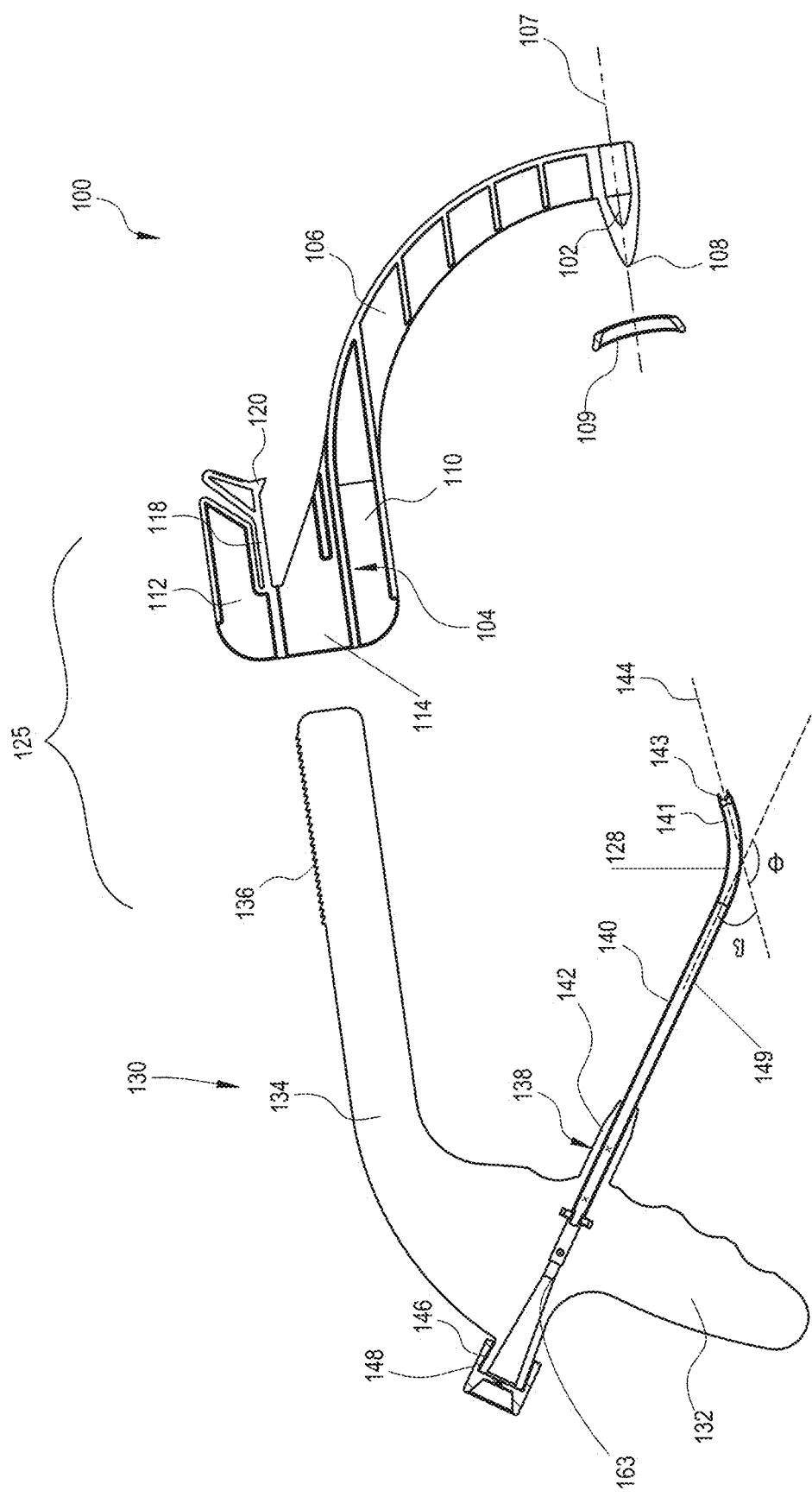

Reference is now made to FIGS. 1A & 1B, which are a simplified exploded view illustration and sectional view illustration respectively of a guiding device comprised of an exit point fixation assembly and an entry point guiding assembly, section being taken along lines A-A in FIG. 1A, the guiding device constructed and operative in accordance with some embodiments of the present invention.

It is seen in FIGS. 1A & 1B that the guiding device comprises a frame comprising at least two parts including a drill entrance side part 190 and a drill exit side part 195. In some embodiments, the drill exit side part comprises an exit point fixation assembly 100 is preferably and optionally an integrally formed element, optionally made of plastic and includes a fixation tip portion 102, a connection portion 104 and a bridge portion 106, joining the fixation tip portion 102 and the connection portion 104.

It is seen that the fixation tip portion 102 extends longitudinally at a angle (α) from and in respect to a longitudinal axis of an end 122 of bridge portion 106 located at an opposite end of bridge 106 from connection portion 104 and is arranged along longitudinal axis 144 extending from cannula tip 127 to fixation tip portion fixation tip 150. In some embodiments, angle (α) may be between 30 and 120 degrees, between 60 and 90 degrees, between 45 and 60 degrees, less than 30 degrees or more than 120 degrees. In some embodiments, the angle is a right angle in respect to end 122 of bridge portion 106. Fixation tip portion 102 preferably includes a tip 108 having a sharp end 150 and adapted to be attached to a securing element 109 that is positioned and fixed against the skin of a patient.

It is further seen in the example depicted in FIGS. 1A & 1B that connection portion 104 includes a first longitudinal portion 110 and a second longitudinal portion 112 generally extending in parallel to the first longitudinal portion 110 and is separated therefrom by an opening 114 defined by a circumferential wall 116.

In some embodiments, connection portion 104 may include a sliding coupling. In the embodiment depicted in FIGS. 1A and 1B the sliding coupling comprises a ratchet-type sliding coupling 125. In some embodiments, ratchet-type sliding coupling 125 comprises a stopper 124. In some embodiments, stopper 124 may comprise a radially deflectable element 118 that may extend adjacent to second longitudinal portion 112 and include a ratchet tooth 120 at its end. It is noted that the second longitudinal portion 112 serves as a stopper for excessive radial deflection of radially deflectable element 118 when not in use.

It is a particular feature of an embodiment of the present invention that the first longitudinal portion 110, second longitudinal portion 112 and fixation tip portion 102 all extend along longitudinal axes (e.g., longitudinal axis 126) which are parallel to longitudinal axis 144.

It is further seen in FIGS. 1A & 1B that in some embodiments, the drill guide comprises a drill entrance side part comprising an entry point guiding assembly 130, preferably and optionally integrally made of a plastic material and preferably and optionally gun-shaped to allow ergonomically convenient hand grip by the user. Entry point guiding assembly 130 comprises a gripping portion 132 and a longitudinal connecting portion 134. One or more ratchet cooperating teeth 136 are disposed on a portion of connecting portion 134.

It is further seen that in some embodiments, gripping portion 132 comprises a hollow drill insertion tunnel 138 that protrudes through gripping portion 132 and extends at an angle (β) in respect to longitudinal axis 144.
In some embodiments, angle (β) may be between 30 and 120 degrees, between 60 and 90 degrees, between 45 and 60 degrees, less than 30 degrees or more than 120 degrees. In some embodiments, angle (β) is defined by the angle (Φ) of the curvature of curved portion 128. The drill insertion tunnel 138 holds a preferably and optionally metal cannula 140, a proximal end of which is enclosed by the drill insertion tunnel 138 a distal end 141 and optionally a curve mid-portion 128 of the cannula 140 extends distally from a distal end 142 of the drill insertion tunnel 138 and optionally comprises a plurality of spikes 143 on distal end 142 tip 127 adapted to be engaged with the bone of a patient. Tip 127 corresponds to the bone entry point of the drill into the bone. In some embodiments, an angle (Φ) between the longitudinal axis of the straight proximal portion 149 of cannula 144 and the longitudinal axis of the straight distal end 141 distal to the curved portion defines the degree of curvature of the curved portion. In some embodiments, an angle (Φ) between the longitudinal axis of the straight proximal portion of the cannula and the longitudinal axis of the straight distal end distal to the curved portion defines the degree of curvature of the curved portion. In some embodiments, angle (Φ) between the longitudinal axis of the straight proximal portion of the cannula and the longitudinal axis of the straight distal end distal to the curved portion is between 90 and 180 degrees, 120 and 150 degrees, 130 and 140 degrees, more than 180 degrees or less than 90 degrees. In some embodiments, angle (Φ) is 45 degrees.
The cannula 140 is retained within the drill insertion tunnel 138 and is adapted for insertion of a guide pin therethrough. The distal end 141 of cannula 140 distal to curved portion 128 extends along axis 144.

As particularly seen in the exemplary embodiment shown in FIG. 1B, drill insertion tunnel 138 comprises a proximal end 146 and distal end 142. It is particularly seen in FIGS. 1A & 1B that tunnel 138 may optionally comprise a sealing diaphragm 148 mounted onto the proximal end 146 of drill insertion tunnel 138. The sealing diaphragm 148 may be attached to the drill insertion tunnel 138 or integrally made therewith, by means of over molding for example.

Securing element 109 is preferably and optionally shaped as a positioning ring, as particularly seen in detail A in the exemplary embodiment depicted in FIG. 1A and is attached to tip 108 of fixation tip portion 102. The securing element 109 comprises sharp end 150 adapted for positioning against the bone of a patient. The securing element 109 preferably allows a guide pin to pass therethrough while drilling.

It is noted that securing element 109 is attached to tip 108 in a bearing-type connection, enabling the securing element 109 to pivot and adjust its orientation with respect to fixation tip portion 102 in order to comply with the curvature of the surgical site.

It is noted and particularly seen in exemplary embodiment illustrated in FIG. 1A that cannula 140 is preferably and optionally adapted to be enclosed by a protective sleeve 160, preferably and optionally made of an elastomeric material. It is appreciated that the protective sleeve 160 comprises a cut 162 formed thereon, enabling the user to pull the protective sleeve 160 proximally in order to expose the spikes 143 of the cannula 140 and allow positioning of the guiding device with respect to the bone of the patient. It is noted that protective sleeve 160 is optionally made of a plastic material, such as PVC for example and is utilized for protecting the patient tissues from injury.

It is further specifically seen in FIG. 1B that a lumen 163 is formed within drill insertion tunnel 138, the lumen 163 is optionally sealed at the proximal end 146 by the sealing diaphragm 148.

Figure 2:
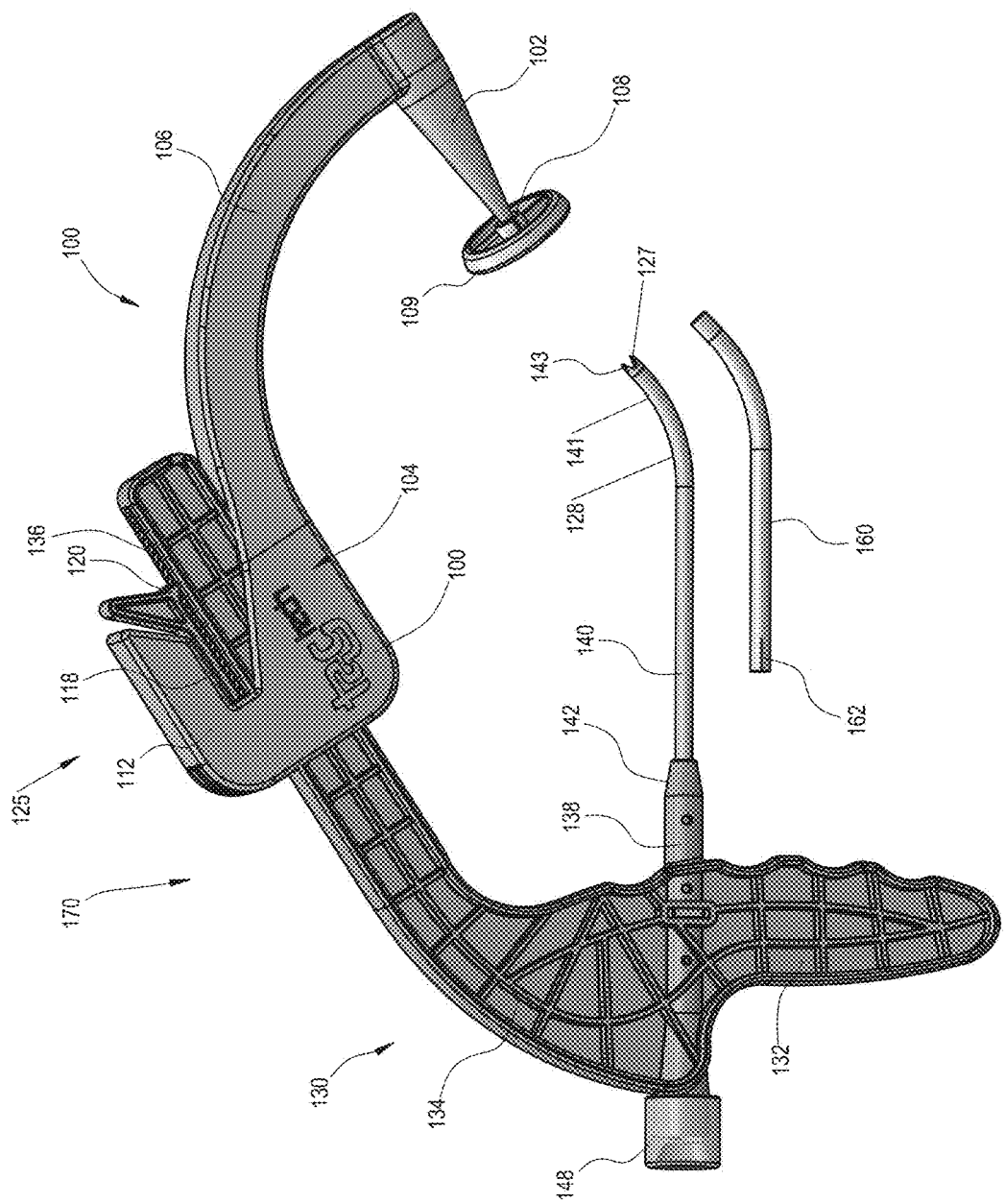
FIG. 2 is a partially assembled simplified pictorial view illustrations of the guiding device of FIGS. 1A & 1B.
Figure 3:
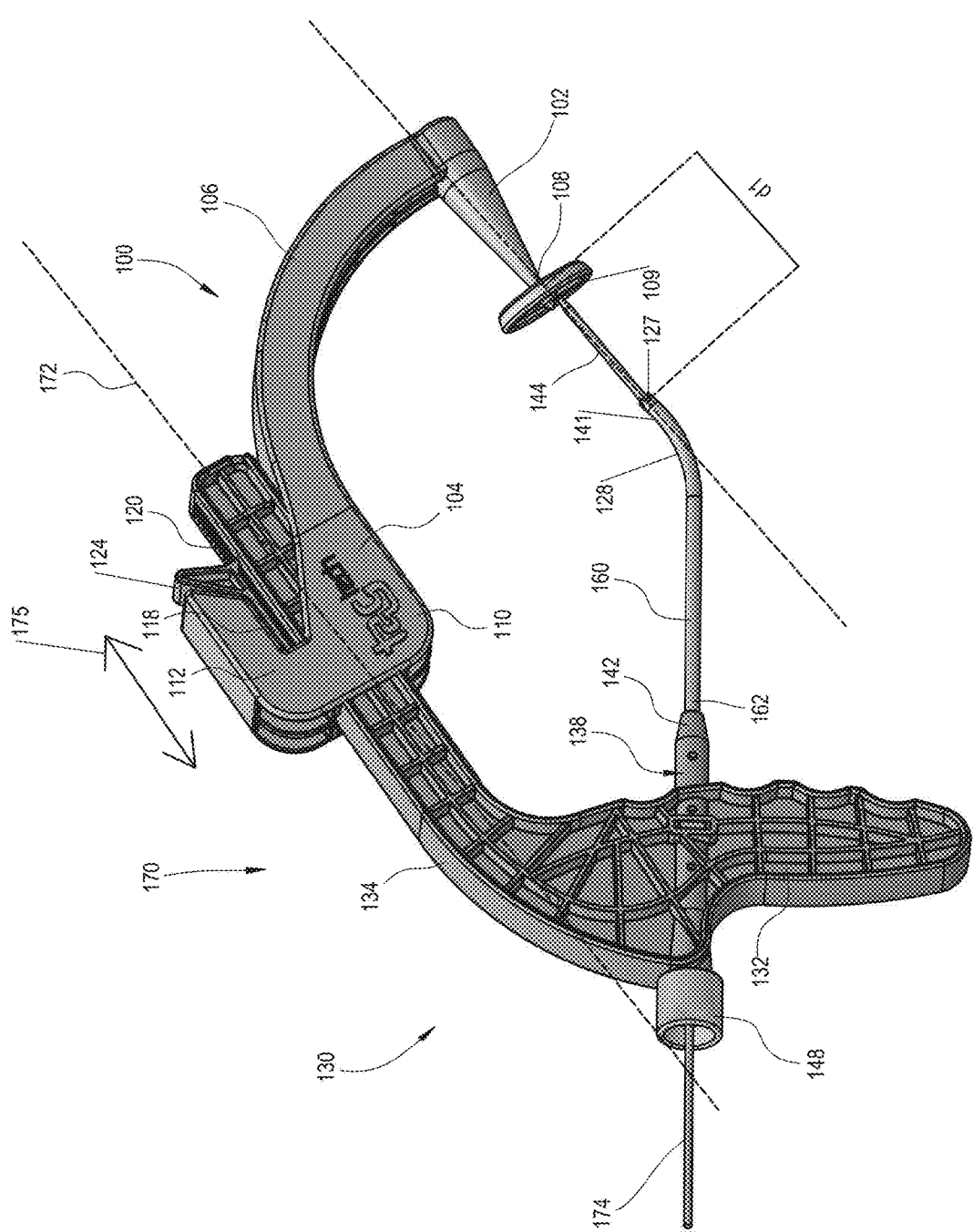
FIG. 3 is an assembled simplified pictorial view illustrations of the guiding device of FIGS. 1A & 1B showing a guide pin inserted therethrough.

Reference is now made to FIG. 2, which is a partially assembled simplified pictorial view illustration of a guiding device similar to the devices shown in FIGS. 1A & 1B and to FIG. 3, which is an assembled simplified pictorial view illustration of a guiding device similar to the devices shown in FIGS. 1A & 1B showing a guide pin inserted therethrough.

An assembled guiding device 170 is seen in the exemplary embodiments shown in FIGS. 2 & 3. It is seen that the entry point guiding assembly 130 is inserted into the exit point fixation assembly 100, such that connecting portion 134 is at least partially inserted into opening 114 (FIG. 1B) of exit point fixation assembly 100, thus the ratchet locking tooth 120 of stopper 124 is engaged with one or more ratchet cooperating teeth 136 and the exit point fixation assembly 100 is selectively locked with respect to entry point guiding assembly 130. In some embodiments, raising stopper 124 such that locking tooth 120 disengages ratchet cooperating teeth 136 to allow axial sliding of entry point guiding assembly 130 and exit point fixation assembly 100 towards and away each other as depicted by double headed arrow 175 along longitudinal axis 172. In the exemplary embodiment depicted in FIG. 3 longitudinal axis 172 is parallel to axis 144 that joins longitudinal axes of fixation tip portion 102 and distal end 141 of cannula 140. In some embodiments, movement of entry point guiding assembly 130 and exit point fixation assembly 100 towards and away each other along longitudinal axis 172 brings distal end 141 of cannula 140 and fixation tip portion 102 to correspondingly move axially towards and away each other along longitudinal axis 144 and in parallel to ratchet-like coupling 125 longitudinal axis 172.

In some embodiments, ratchet-like coupling 125 reversibly and rigidly couples entry point guiding assembly 130 and exit point fixation assembly 100. When entry point guiding assembly 130 and exit point fixation assembly 100 are coupled ratchet-like coupling 125 locks distal end 141 of cannula 140 and fixation tip portion 102 in place, facing each other, their longitudinal axes forming a single line with longitudinal axis 144, and a distance (d1) between distal end 141 tip 127 (i.e., point of entry of the bone drill into the bone) and tip portion 102 tip 108 is maintained.

A potential advantage of guiding device 170 is in that when assembled, the spatial orientation of distal end 141 tip 127 in respect to tip portion 102 tip 108 is maintained at all instances including movement of device 170 during operation.

Referring back to the exemplary embodiment depicted in FIG. 1A, in some embodiments guiding device 170 securing element 109 comprises a marker that marks an estimated exit point in respect to the drill entry point into the bone marked by tip 127. In accordance with some embodiments of the invention, the drill used may be semi-rigid or flexible to a certain extent and configured to follow a curved path. In some most instances, once the drill protrudes from distal end 141 tip 127 it continues along a straight path towards tip portion 102 tip 108. In some instances, once the drill protrudes from distal end 141 tip 127 it may divert from the straight path in response to various obstacles along the path such, for example, varying bone density, the degree of diversion limited by the bending characteristics of the drill. As a result, the drill may exit in propinquity to but not exactly at tip portion 102 tip 108.

In some embodiments, securing element 109 comprises a marker that defines a perimeter within which the bone drill may exit. The perimeter defined by a ring geometry of marker 109 and is concentrically coupled to fixation tip portion 102 such that tip 108 comprises the center of marker/securing element 109. The radius of marker/securing element 109 depends on the bending characteristics of the drill. The greater the drill flexibility the greater the radius of marker/securing element 109 and vice versa.

As explained elsewhere herein when entry point guiding assembly 130 and exit point fixation assembly 100 are reversibly rigidly coupled, the spatial orientation of distal end 141 tip 127 in respect to tip portion 102 tip 108 is maintained such that a path of a drill drilling a bore in bone can be expected to generally follow longitudinal axis 144 and exit the bone at a point defined by tip portion 102 tip 108. However, most drills used are not necessarily rigid and in some instances some flexion may occur during drilling diverting the path of the drill in the bone. The ring of securing element 109 defines a perimeter of the expected exit point of the drill from the bone and thus allows passage within the area defined by and within the ring.

A potential advantage of guiding device 170 is in that when assembled and fixed in place, the marker marks an estimated exit point of a drill drilling a bore in the bone with respect to the point of drill entry, within a perimeter defined by the marker.

A potential advantage of guiding device 170 is in that when assembled and fixed in place, an angle of a bore to be drilled may be expected since the longitudinal drilling axis 144 parallels ratchet-like coupling 125 longitudinal axis 172. Moreover, an exit point of a drill to be drilling a bore in the bone and the angle of the bore to be drilled may be estimated during the procedure if for some reason guiding device 170 has moved in respect to the bone. It is appreciated that the guiding device 170 can be adjusted for various bone sizes by means of meshing the ratchet tooth 120 with a different one of ratchet cooperating teeth 136 in accordance with the size of the bone to be drilled.

It is a particular feature of an embodiment of the present invention that once exit point fixation assembly 100 is locked with respect to entry point guiding assembly 130, drilling path between entry point of the drill and exit point of the drill may be estimated.

In the exemplary embodiment depicted in FIG. 2, protective sleeve 160 is seen separately from guiding device 170 and the cannula 140 with spikes 143, which are adapted to be engaged with the bone of the patient, can be clearly seen. In the exemplary embodiment depicted in FIG. 3, protective sleeve 160 is mounted onto cannula 140 in order to protect the patient tissues from injury while drilling.

It is a particular feature of an embodiment of the present invention that as seen particularly in the exemplary embodiment depicted in FIG. 3, fixation tip portion 102 and distal end 141 of cannula 140 are adapted to be arranged along a single mutual longitudinal axis, such as longitudinal axis 144 once the entry point guiding assembly 130 and exit point fixation assembly 100 are reversibly rigidly coupled.

It is seen in FIG. 3 that connecting portion 134 of entry point guiding assembly 130 is arranged along a single mutual longitudinal axis 144 with connecting portion 104 of the exit point fixation assembly 100.

It is a further particular feature of an embodiment of the present invention that as further seen particularly in FIG. 3, once the entry point guiding assembly 130 and exit point fixation assembly 100 are attached longitudinal axes 144 and 172 extend in parallel to each other, thus fixating the relative angle of distal end 141 of cannula 140 with respect to the bone of the patient and additionally fixating the relative angle of the fixation tip portion 102 with respect to the bone of the patient.

It is particularly seen in FIG. 3 that a guide pin 174 having a drilling head 176 (FIG. 9) is inserted through the sealing membrane 148, through lumen 163 and is mainly enclosed by the protective sleeve 160 before drilling. The guide pin 174 is preferably and optionally made of shape-memory material, such as for example, Nitinol and thus can be bent within the cannula 140 to comply with the curved shape of the cannula and straightened once the guide pin 174 protrudes distally out of the curved distal end 141 of cannula 140.

It is a particular feature of an embodiment of the present invention that the drilling angle is defined by the exit angle of the guide pin 174 from the distal end 141 of cannula 140.

It is noted that the sealing membrane 148 is perforated by insertion of the guide pin 174 therethrough, but provides fluid sealing such as preventing bleeding past lumen 163.

A method of using guiding device 170 is particularly shown in the exemplary embodiments depicted in FIGS. 4-9.

Figure 4:
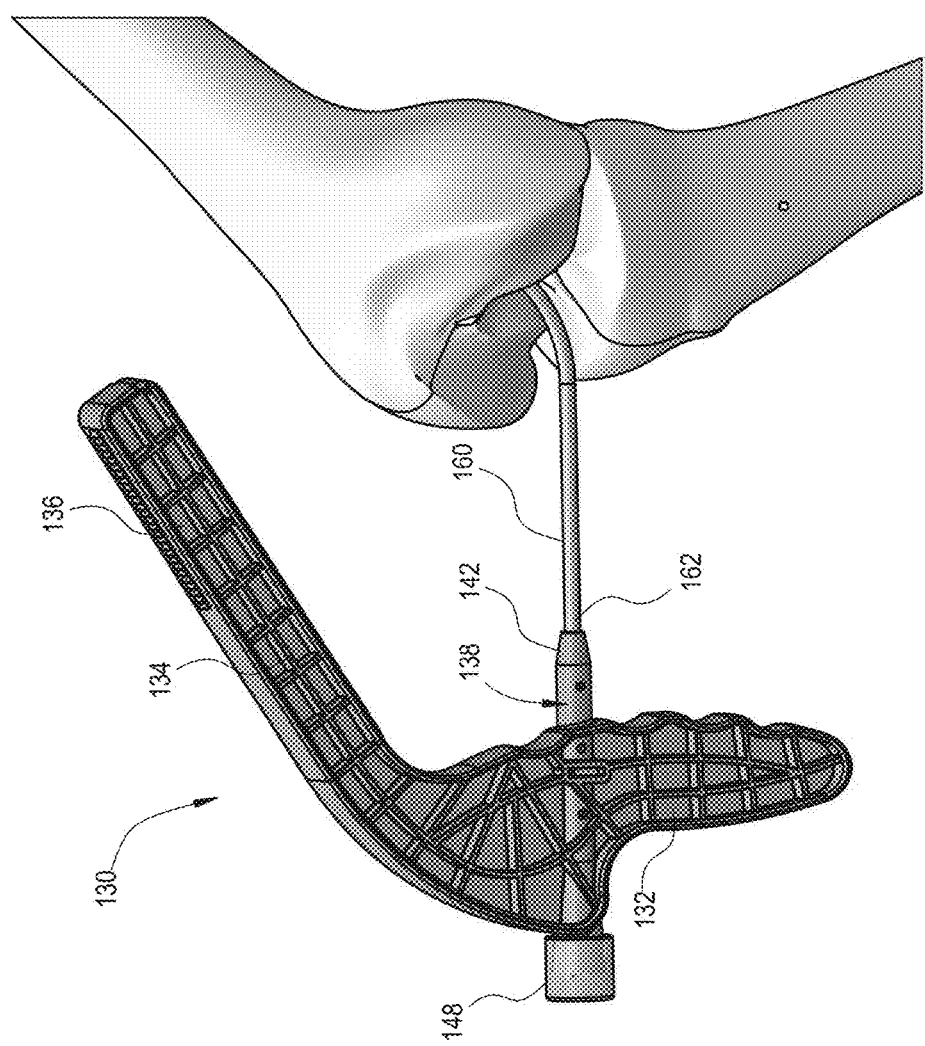
FIG. 4 is a simplified pictorial illustration of the entry point guiding assembly engaging a bone of a patient.

Reference is now made to FIG. 4, which is a simplified pictorial illustration of the entry point guiding assembly 130 engaging a bone of a patient.

First step of using the guiding device 170 includes defining the entry point of the guide pin 174 by means of engaging the entry point guiding assembly 130 to the bone of the patient.

Figure 5:
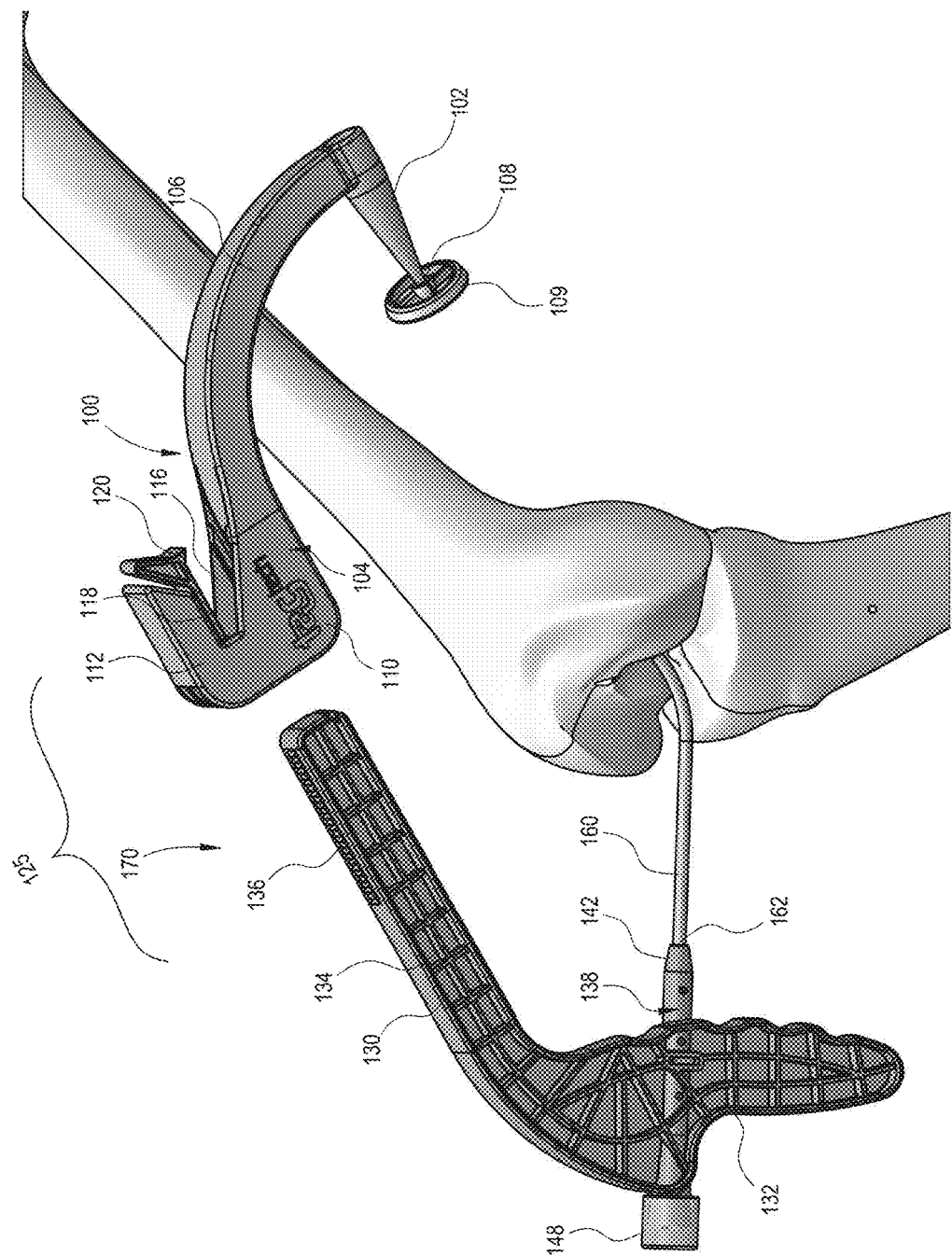
FIG. 5 is a simplified pictorial view illustration of positioning the exit point fixation assembly with respect to the skin of the patient.

Reference is now made to FIG. 5, which is a simplified pictorial view illustration of positioning the exit point fixation assembly 100 with respect to the bone of the patient.

Second step of using the guiding device 170 includes defining the exit point of the guide pin 174 on the skin of the patient by means of positioning securing element 109 on the skin of the patient. Securing element 109 pivots to comply with the curvature of the skin at the surgical site and the exit point fixation assembly 100 is shown just before engagement with the entry point guiding assembly 130.

In the following FIGS. 6, 7, 8, 9 and 16, for reason of simplicity of explanation, soft tissues have been removed and securing element 109 is shown to be in contact with bone. In practice as explained elsewhere herein and depicted in FIG. 10 guiding device 170 securing element 109 is urged against soft tissue (e.g., skin) over the bone at an expected exit point of the drill.

Figure 6:
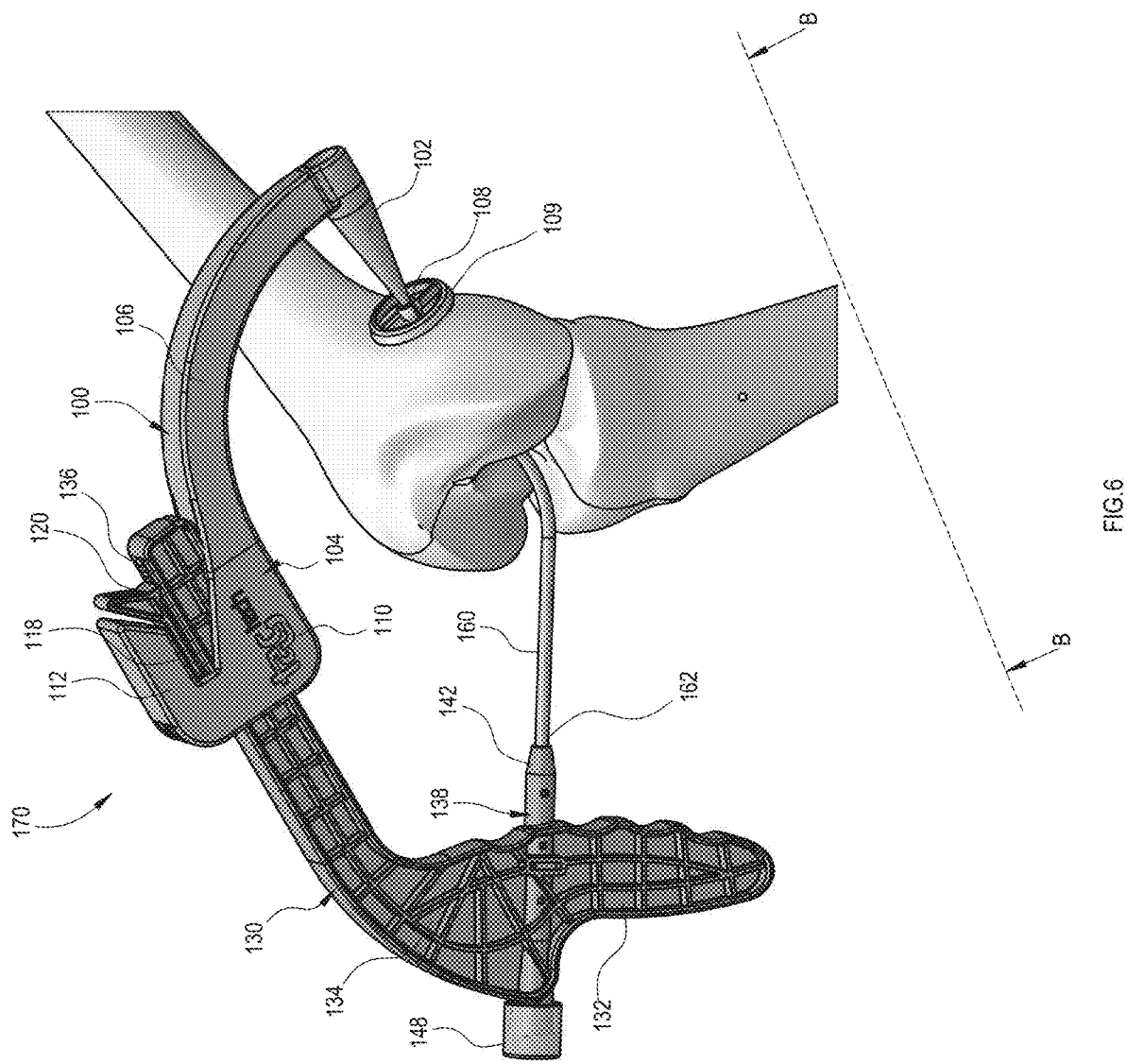
FIGS. 6 & 7 are a simplified pictorial view illustration and a sectional view respectively of fixating the exit point fixation assembly and the entry point guiding assembly with respect to the bone of a patient, section being taken along lines B-B in FIG. 6.
Figure 7:
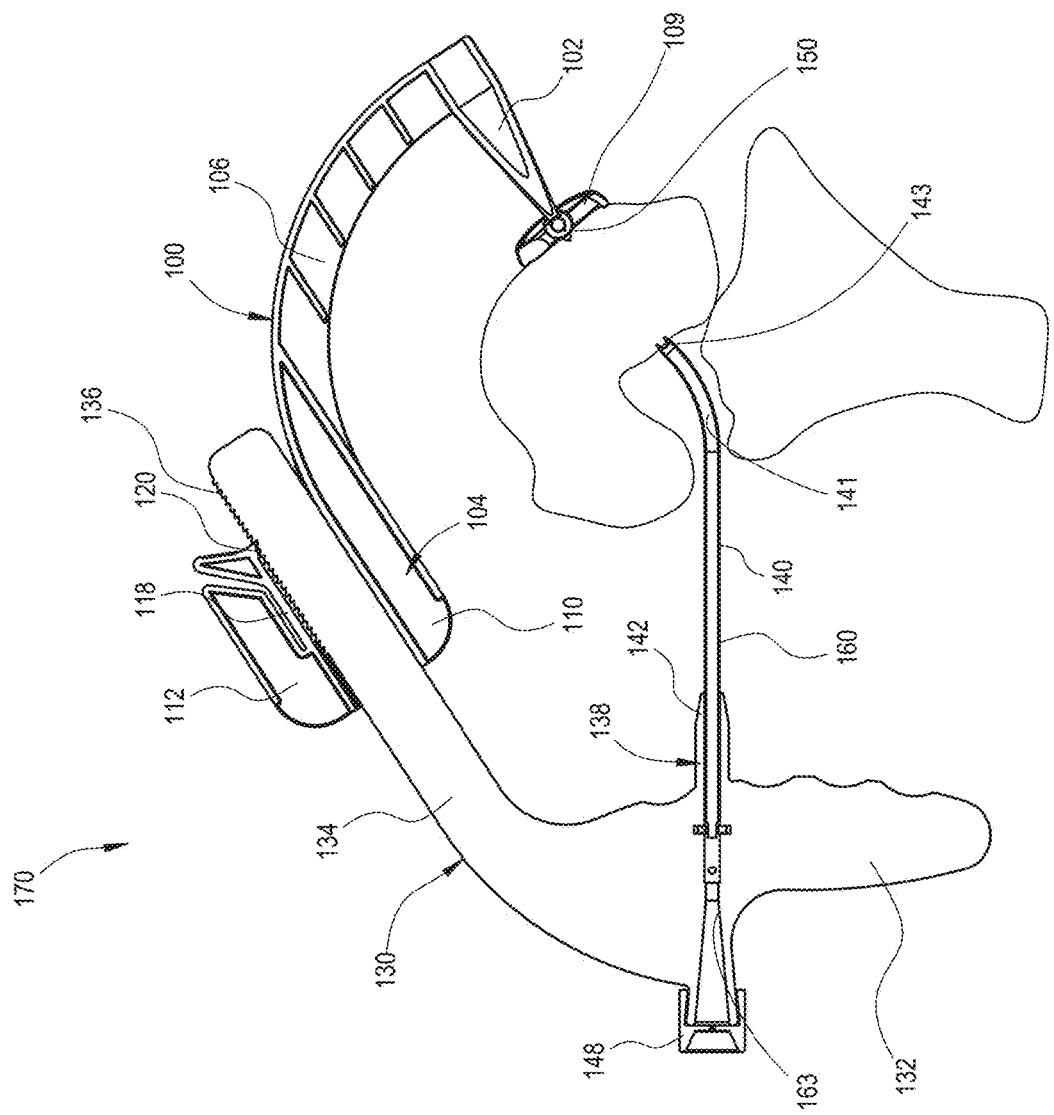

Reference is now made to FIGS. 6 & 7, which are a simplified pictorial view illustration and a sectional view respectively of fixating the exit point fixation assembly 100 and the entry point guiding assembly 130 with respect to the bone of a patient, section being taken along lines B-B in FIG. 6.

Third step of using the guiding device 170 includes securely engaging the exit point fixation assembly 100 with entry point guiding assembly 130 by means of meshing the ratchet tooth 120 with ratchet cooperating teeth 136 such that the guiding device 170 is locked with respect to the bone of the patient.

It is particularly seen in FIG. 7 that spikes 143 of cannula 140 are engaged with the bone of the patient at the entry point. The sharp end 150 of securing element 109 is engaged with the skin of the patient at the surgical site. The diaphragm 148 seals the lumen 163 at this stage of operation.

Figure 8:
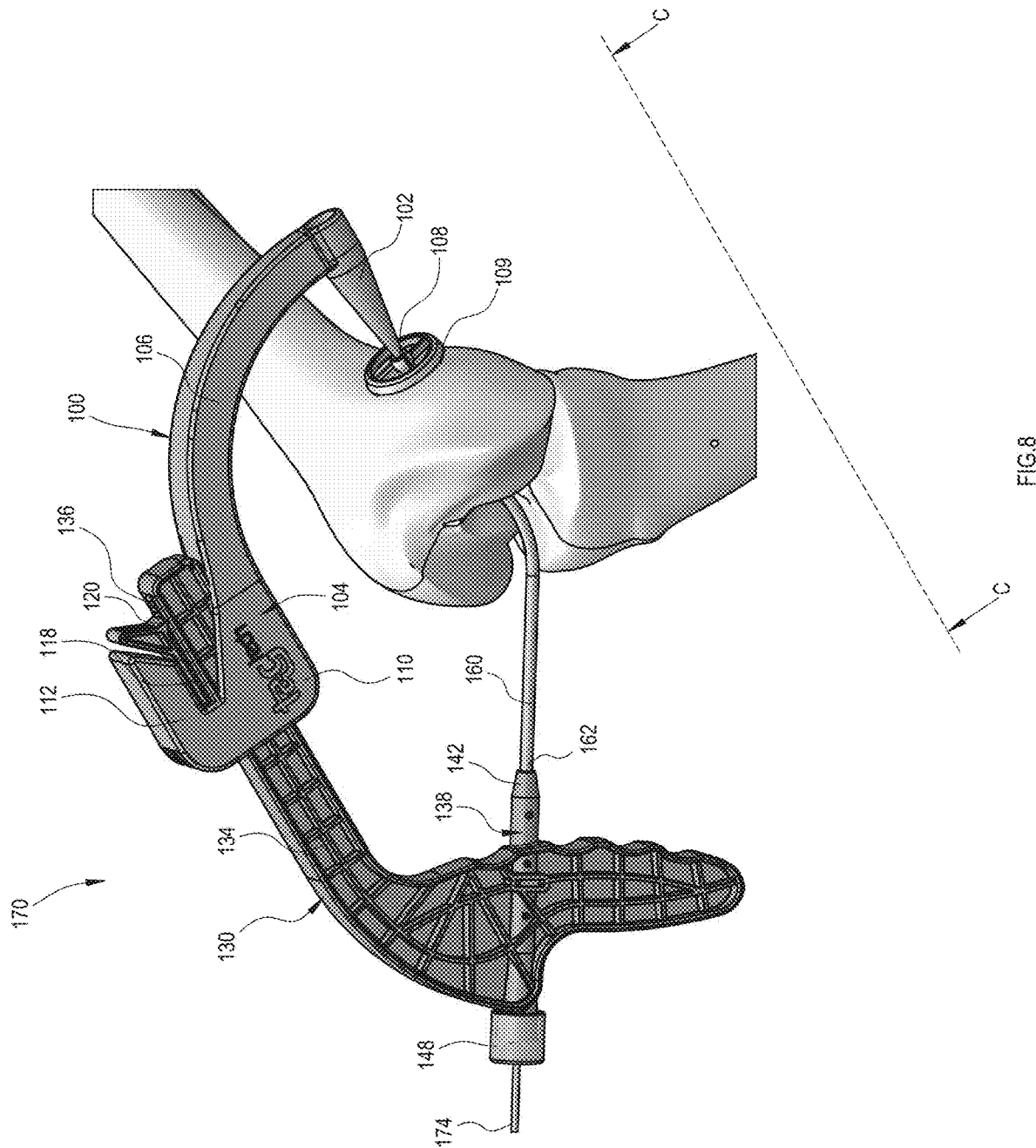
FIGS. 8 & 9 are a simplified pictorial view illustration and a sectional view respectively of drilling through the guiding device of FIGS. 1A & 1B, section being taken along lines C-C in FIG. 8.
Figure 9:
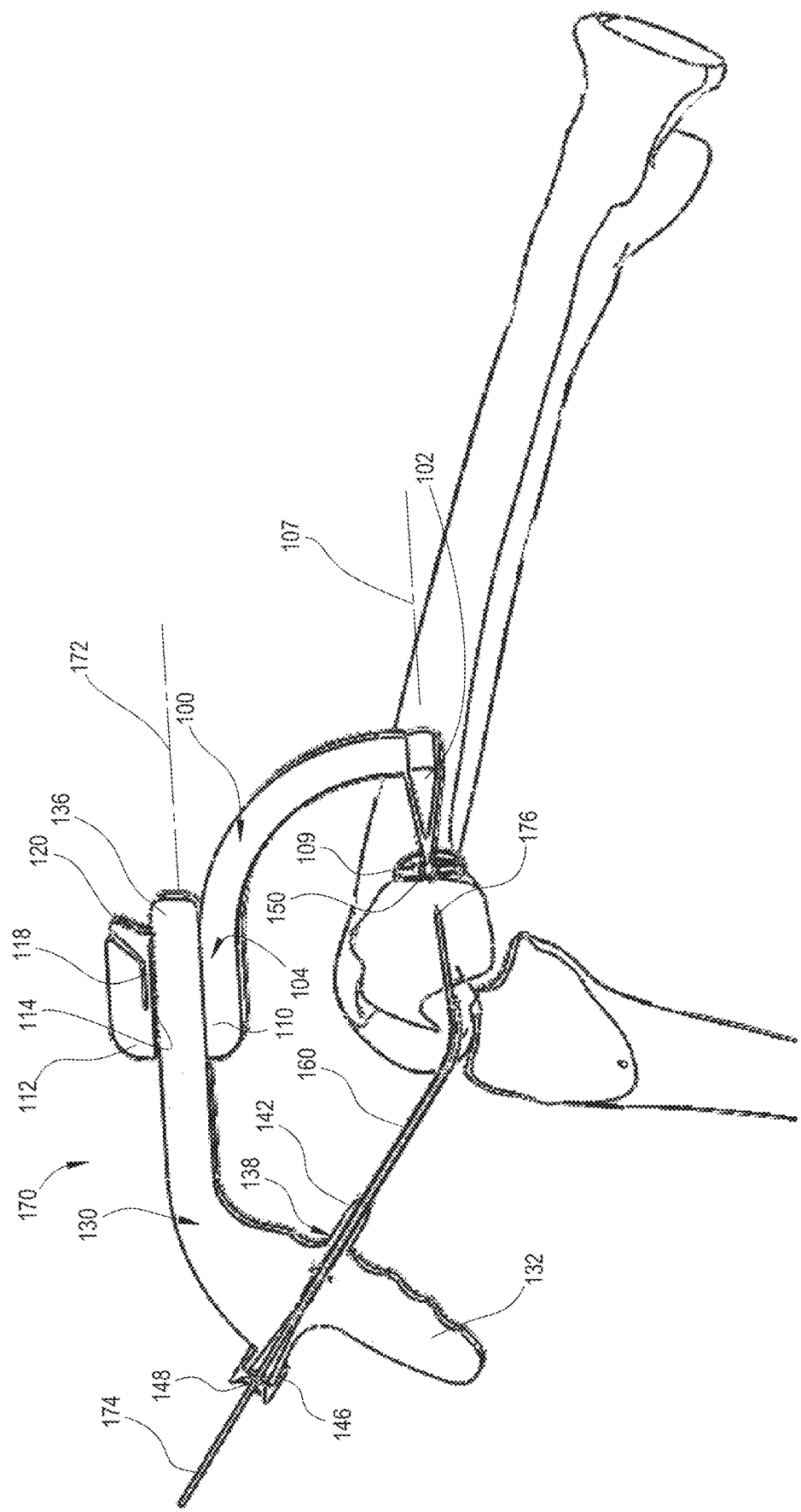

Reference is now made to FIGS. 8 & 9, which are a simplified pictorial view illustration and a sectional view respectively of drilling through the guiding device 170 of FIGS. 1A & 1B, section being taken along lines C-C in FIG. 8.

Fourth step of using the guiding device 170 includes inserting a guide pin 174 through diaphragm 148 and thereby perforating it, further inserting the guide pin through lumen 163, cannula 140, straight distal end 141 of cannula 140 and eventually inserting the drilling head 176 of guide pin 174 into the bone of the patient in order to drill an initial bore within the bone of the patient.

It is noted that in this stage, the user has pulled the protective sleeve 160 proximally and exposed the spikes 143 of cannula 140, thus securely fixating the guiding device 170 onto the bone of the patient.

It is particularly seen in FIG. 9 that the drilling head 176 of guide pin protrudes distally from the distal end 141 of cannula 140 and the guide pin 174 has drilled a bore through the bone of the patient. At this stage, the drilling head 176 of guide pin 174 engages the sharp end 150 of securing element 109 or alternatively is partially passed within the area defined by the ring of the securing element 109.

It is appreciated that the guiding device 170 in accordance with an embodiment of the present invention can be fully disposable following a single surgical procedure.

Figure 10:
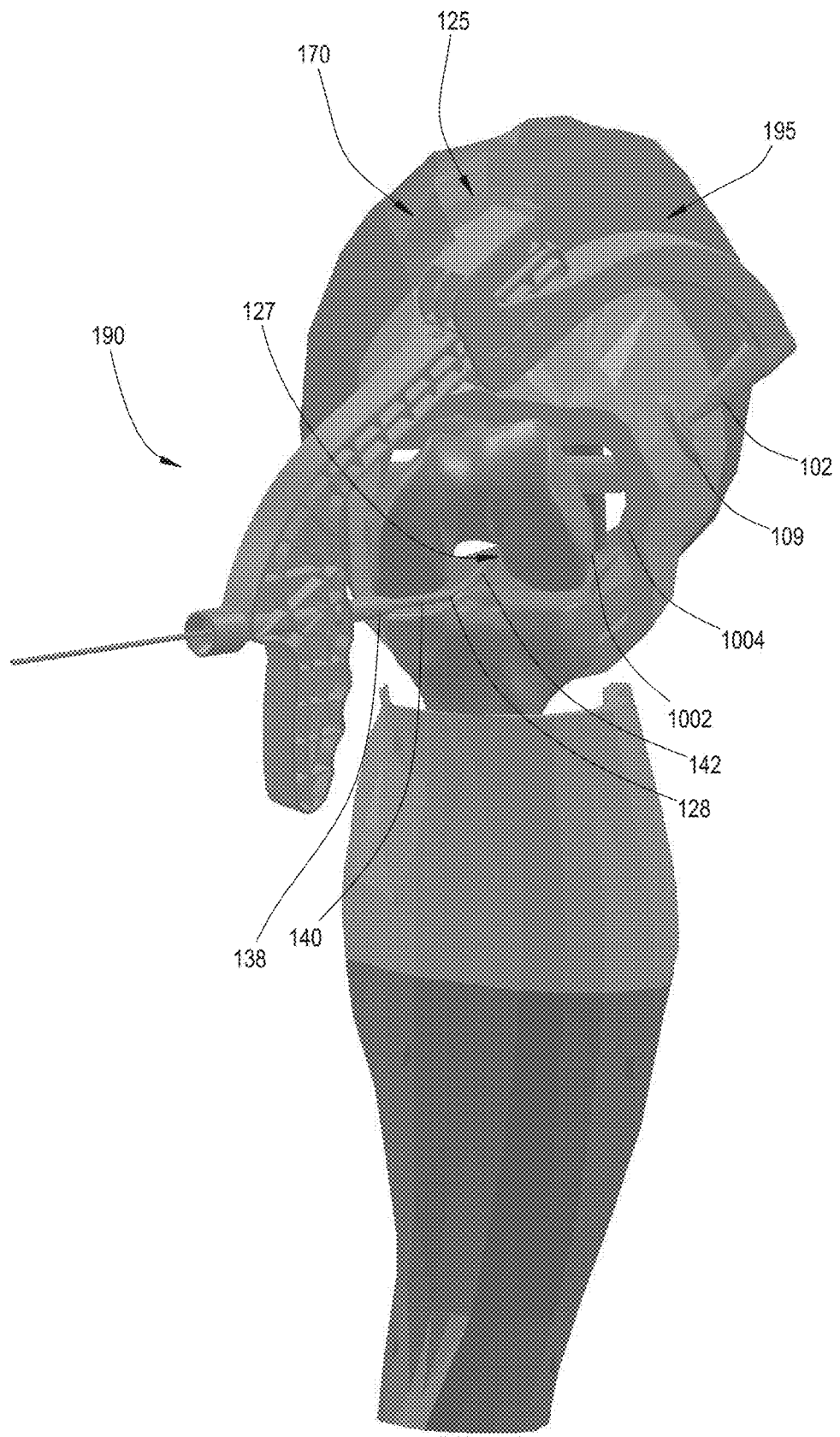
FIG. 10 is a simplified pictorial view of implementation of a drill guide device.

Reference is now made to FIG. 10, which is a simplified pictorial illustration of implementation of a bone drill guide in accordance with some embodiments of the invention. As shown in the embodiment depicted in FIG. 10, drill guiding device 170 comprises a frame comprising a drill entrance side part 190 and a drill exit side part 195 movably coupled. In some embodiments, the drill entrance side part comprises at least a drill insertion guide comprising a drill insertion tunnel 138 and a cannula 140. In some embodiments, a portion of cannula 140 comprises a curved portion 128 and comprises a straight distal end 142 and a tip 127. As shown in FIG. 10, drill exit side part 195 comprises tip portion 102 having a securing element 109. In some embodiments, drill entrance side part 190 and drill exit side part 195 are movably coupled via coupling 125. In practice, cannula tip 127 is placed against a bone 1002 and drill exit side part 195 is coupled and axially moved via coupling 125 towards drill entrance side part 190 until securing element 109 is urged against skin 1004 over bone 1002. Once cannula tip 127 and securing element 109 are in place, coupling 125 is locked and the procedure commenced.

Figure 11A:
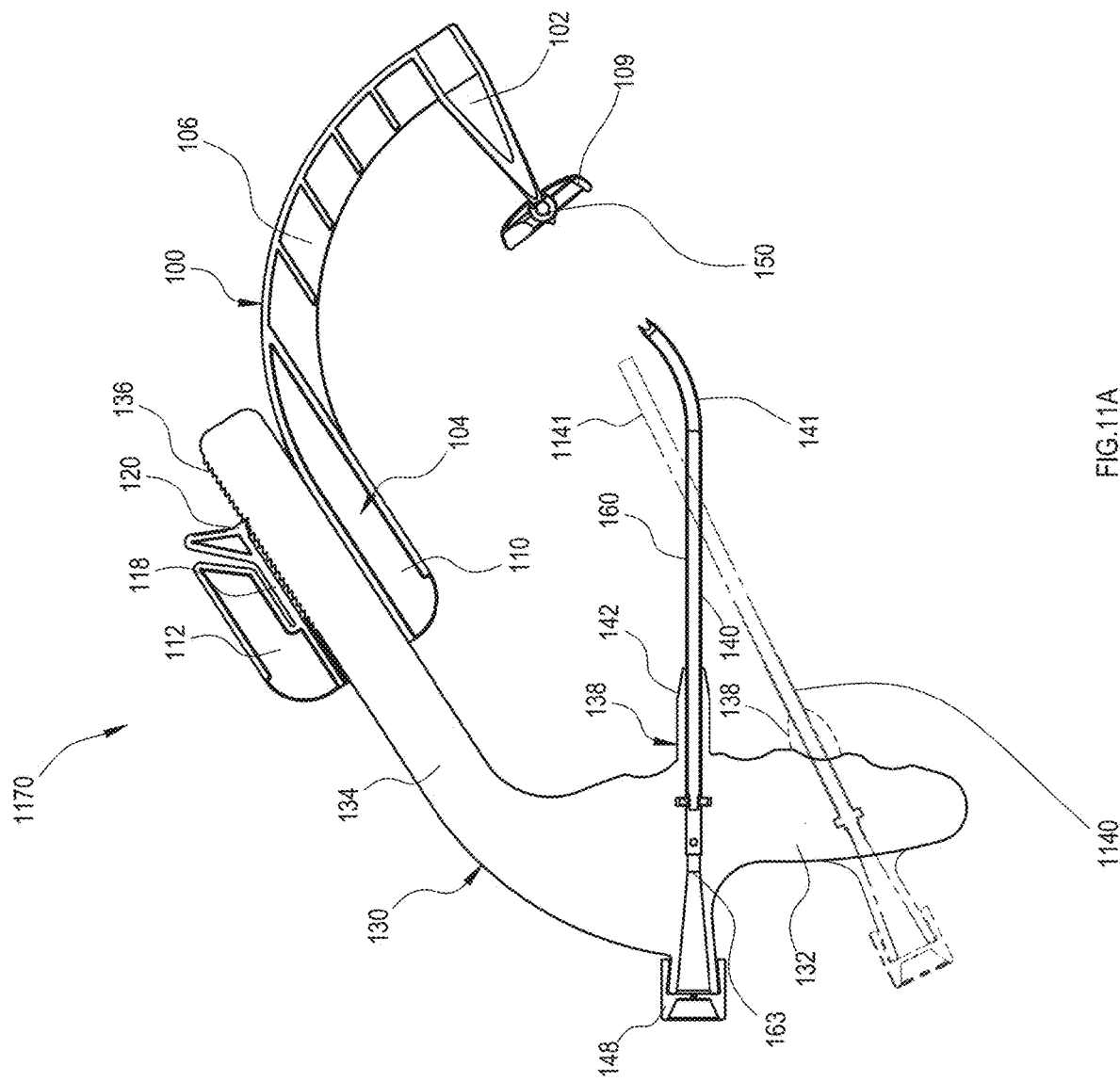
FIGS. 11A & 11B are cross-section views simplified illustration of a drill guiding device in accordance with some embodiments of the present invention.
Figure 11B:
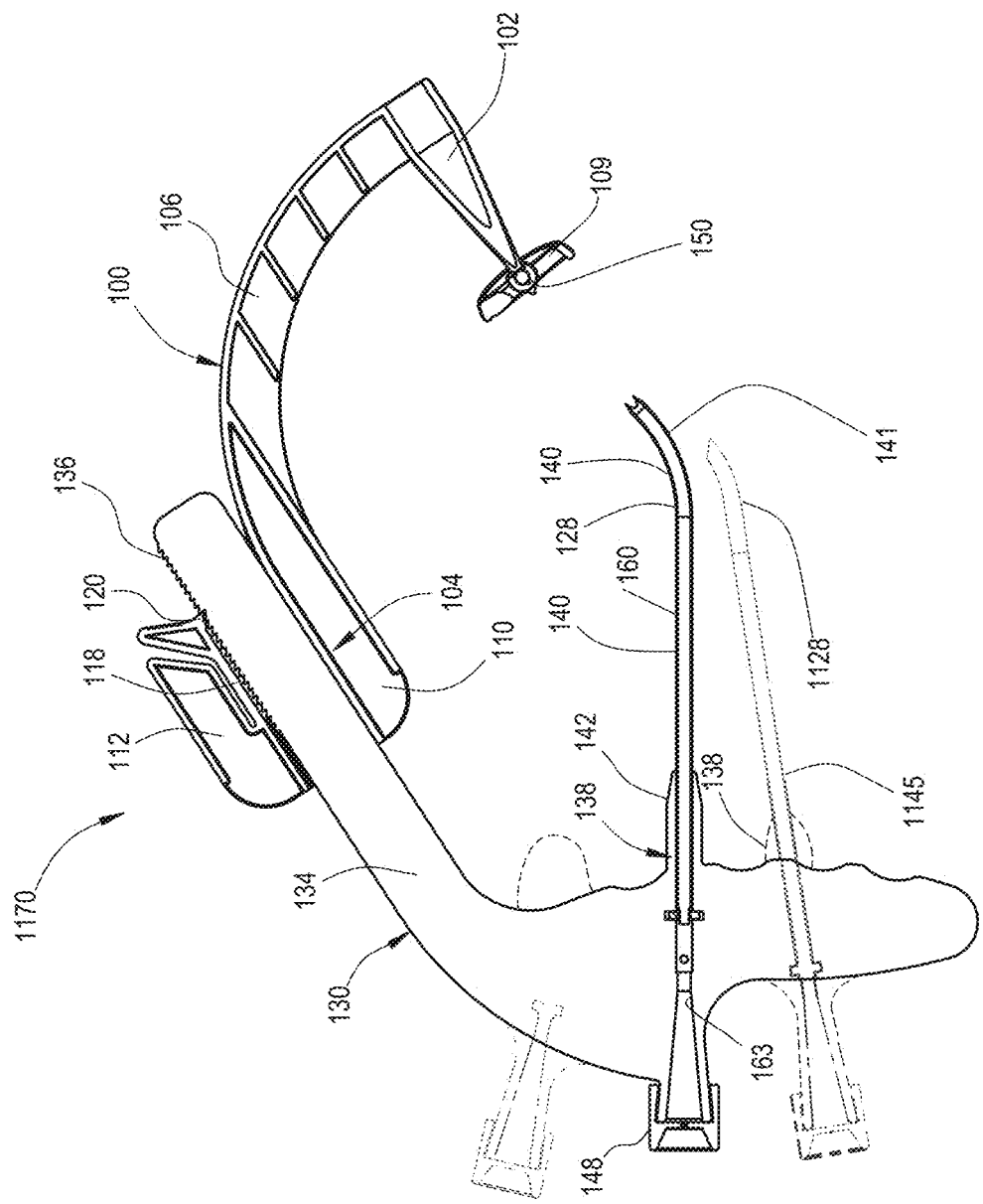

Reference is now made to FIGS. 11A and 11B, which are cross-section view simplified illustrations of a guiding device 1170 in accordance with some embodiments of the present invention. As shown in the optional exemplary embodiment shown in FIG. 11A, guiding device 1170 may be a multiple angle drill guiding device comprising two or more drill insertion tunnels 138 in gripping portion 132 of entry point guiding assembly 130. In some embodiments, drill insertion tunnels 138 are operative to accommodate one or more cannulas 1140/140 at various angles as suitable for a surgical procedure to be performed. In FIG. 11A, an optional drill insertion tunnel 138 and cannula 1140 are depicted with phantom lines. As explained elsewhere hereinabove, guiding devices 170/1170 provide an estimated exit point of a drill drilling a bore in bone, the exit point defined by a single longitudinal axis 144 mutually shared by distal end 141 and tip portion 102. In the examples described elsewhere herein, some surgical orthopedic procedures e.g., Anterior Cruciate Ligament Reconstruction (ACL) procedures, require approaching the drilling site at an angle. This dictates a distal portion of a cannula 140 to be curved. However, other procedures may enable a straight approach and not require an angled approach allowing the use of a straight distal end 1141 cannula such as cannula 1140 shown in FIG. 11A.

To maintain distal end 1141 of straight cannula aligned with along axis 144 with tip portion 102, cannula 1140 may be positioned such that the longitudinal axis of cannula 1140 lies along longitudinal 144.

As shown in the optional exemplary embodiment shown in FIG. 11B, multiple angle drill guiding device 1170 may be suitable for a surgical procedure requiring a shallow angled approach to be performed. In FIG. 11B, an optional drill insertion tunnel 138 and cannula 1140 are depicted with phantom lines. As explained elsewhere hereinabove, guiding devices 170/1170 provide an estimated exit point of a drill drilling a bore in bone, the exit point defined by a single longitudinal axis 144 mutually shared by distal end 141 and tip portion 102. In the examples described elsewhere herein, some surgical orthopedic procedures e.g., Anterior Cruciate Ligament Reconstruction (ACL) procedures, require approaching the drilling site at an angle. This dictates a distal portion of a cannula 140 to be curved. However, other procedures may require a shallow angled approach allowing the use of a cannula such as cannula 1145 shown in FIG. 11B having a shallow angled portion 1128.

To maintain distal end 141 of shallow angled cannula aligned along axis 144 with tip portion 102, cannula 1145 may be positioned such that the longitudinal axis of cannula 1145 is angled at a shallower angle in respect to longitudinal axis 144 than the angle between longitudinal axis of cannula 140 and longitudinal 144.

In some embodiments, two or more drill insertion tunnels 138 are arranged in gripping portion 132 of drill entry side part 190 at varying angles ($\beta_1, \beta_2 \ldots \beta_n$) in respect to axis 144. In some embodiments, each of drill insertion tunnels 138 at angles ($\beta_1, \beta_2 \ldots \beta_n$) corresponds to a single curved cannula having a curved portion curved at a corresponding angle ($\Phi_1, \Phi_2 \ldots \Phi_n$).

Figure 12A:
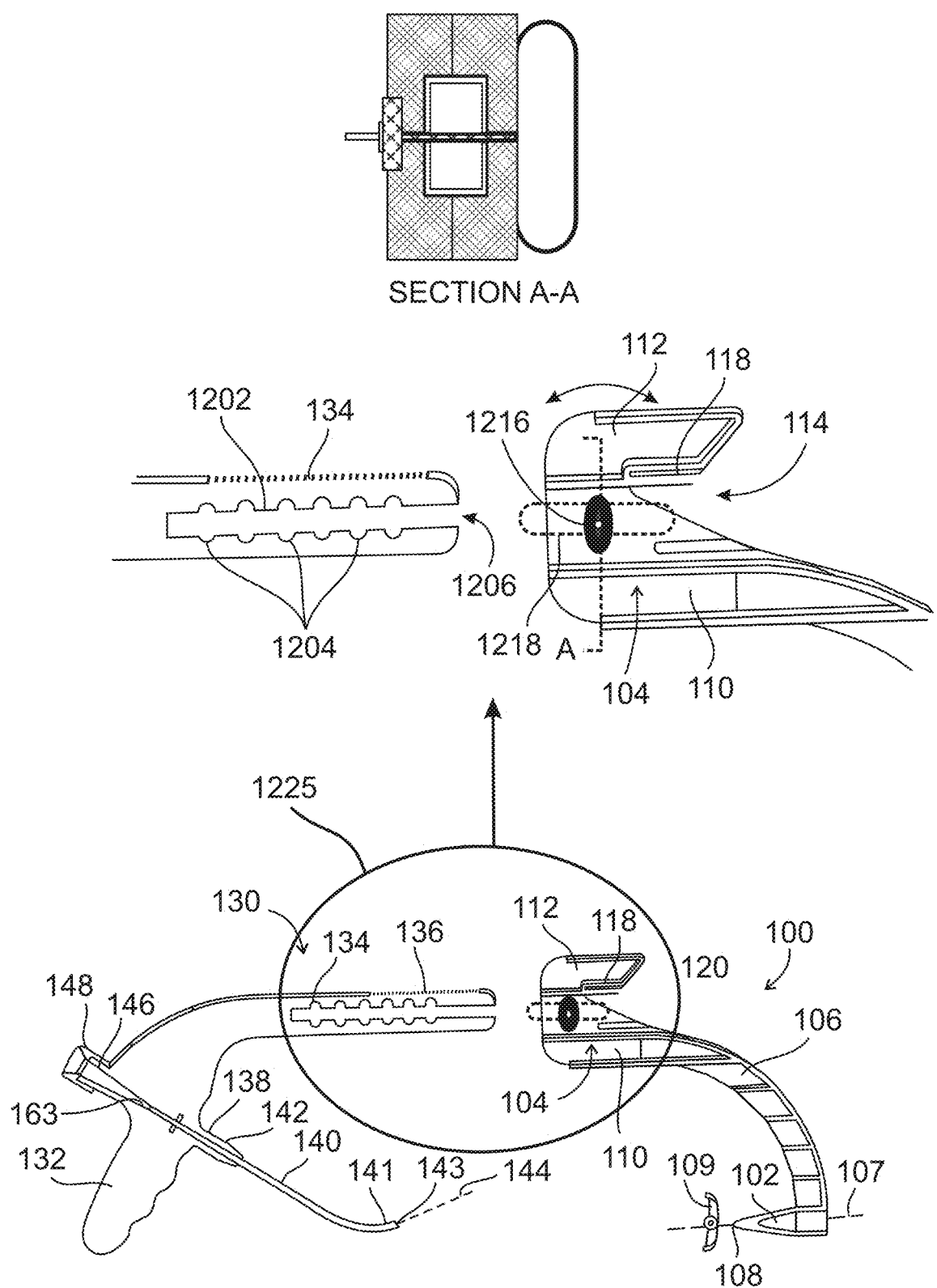
FIGS. 12A to 12D are partial sectional view simplified illustrations of a drill guiding device in accordance with some embodiments of the present invention.
Figure 12B:
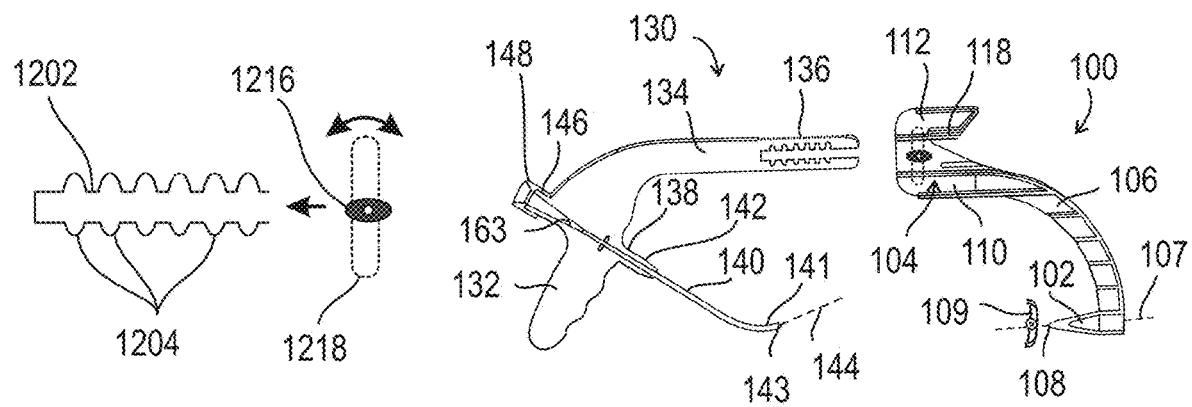
Figure 12C:
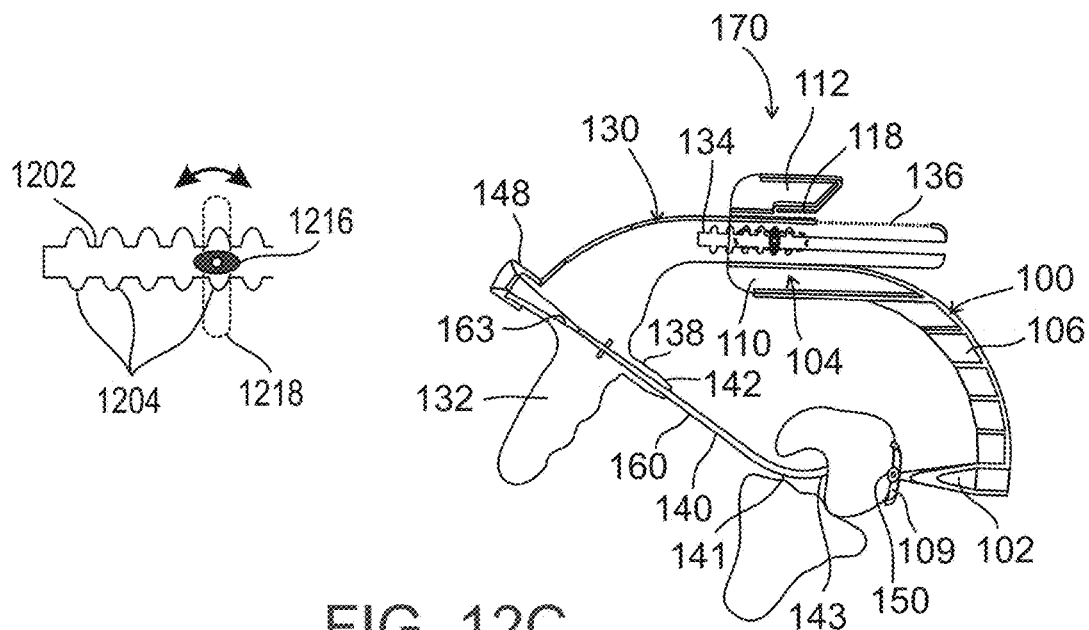
Figure 12D:
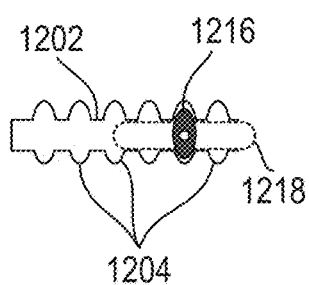
Figure 12D:
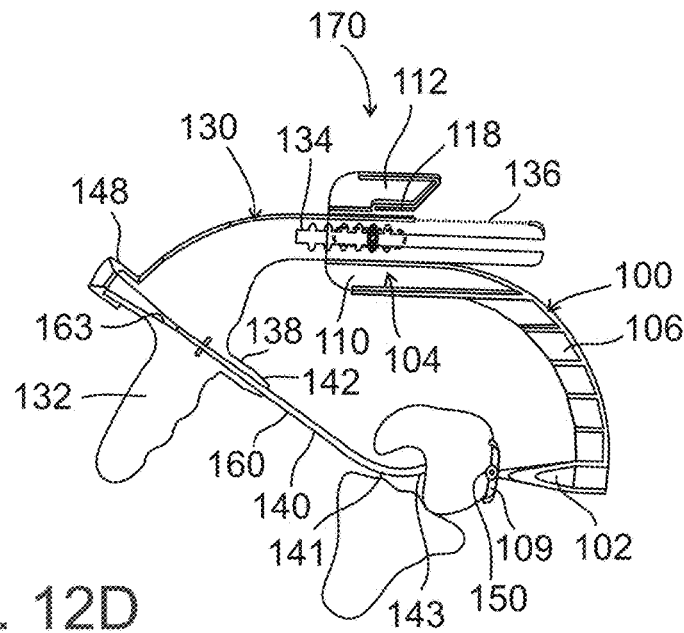

Reference is now made to FIGS. 12A-12D and 13A-13B, which are pictorial and cross section view simplified illustrations of some optional embodiments of the sliding coupling 1225 of the drill guiding device in accordance with some examples of the invention. As shown in the exemplary embodiments depicted in FIG. 12A and section A-A thereof, longitudinal connecting portion 134 may include a slot 1202 comprising a plurality of vertically oriented oval recesses 1204 aligned along a groove parallel to the longitudinal axis of portion 134. Slot 1202 is open to an end 1206 of portion 134. In some embodiments, connection portion 104 opening 114 comprises a rotatable oval stopper 1216 controlled by a rotatable lever 1218. In FIG. 12B, rotatable lever 1218 is manipulated to rotate oval stopper 1216 to a horizontal orientation so to render stopper 1216 slidable through slot 1202 to a desired length at which point and as shown in FIGS. 12C and 12D, rotatable lever 118 is manipulated to rotate oval stopper 116 to a vertical orientation so to render coupling 1225 rigidly locked.

Figure 13A:
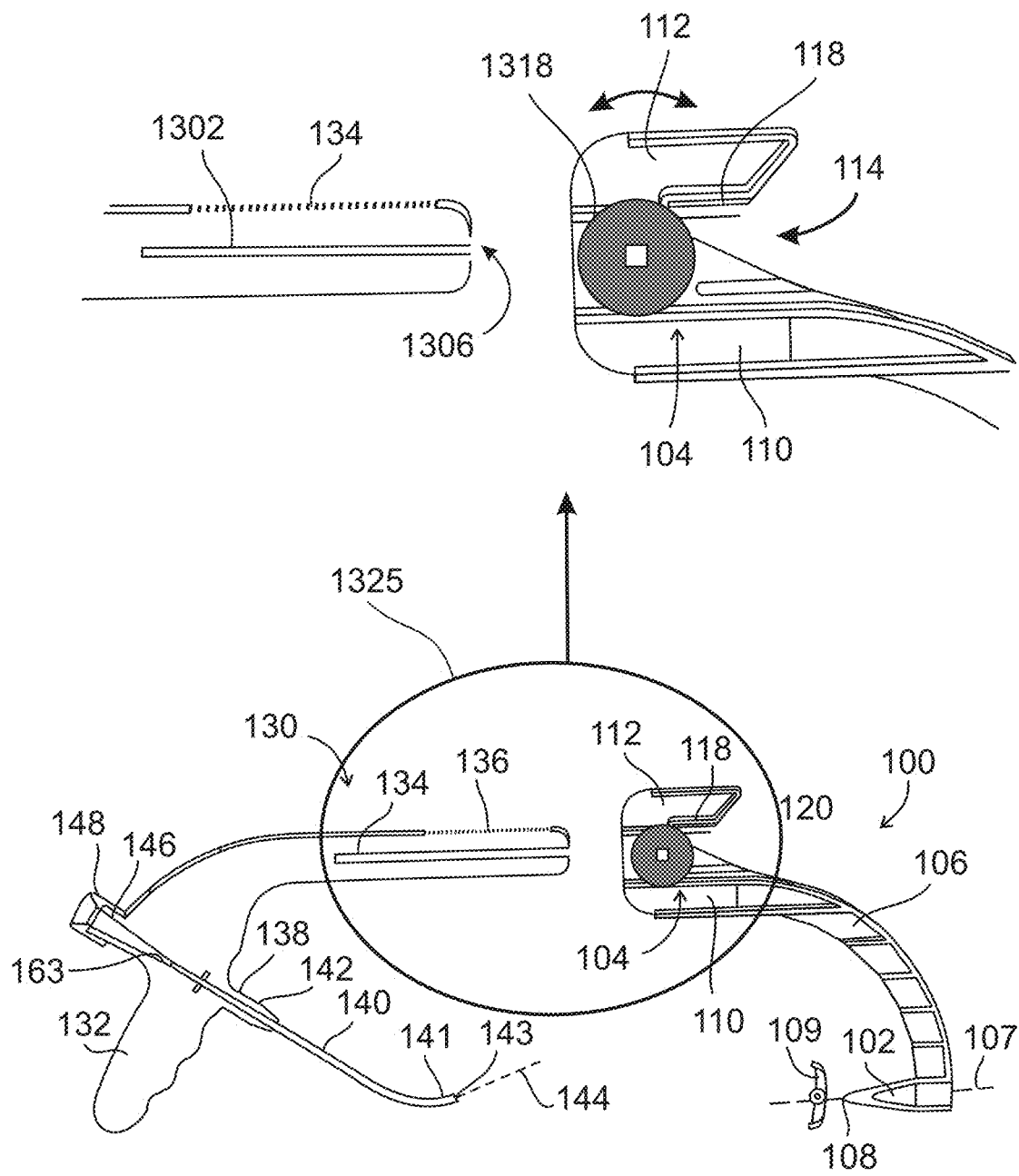

FIG. 13A illustrates a pictorial and cross section view simplified illustrations of an optional embodiment of sliding coupling 1325 examples of the invention. As shown in the exemplary embodiment depicted in FIG. 13A and sections 13B and 13C taken along section G-G, longitudinal connecting portion 134 may include a slot 1302 parallel to the longitudinal axis of portion 134. Slot 1302 is open to an end 1306 of portion 134. In some embodiments, connection portion 104 opening 114 comprises a stopper 1316 controlled by a rotatable wheel 1318. In FIG. 13B, coupling 1325 is shown in an unlocked orientation. As illustrated in FIG. 13C, rotatable wheel 1318 is manipulated to rotatingly drive a shaft 1320 having a threaded end 1322 through a locking bolt 1324 and urging stopper 1316 against longitudinal connecting portion 134 to render coupling 1325 rigidly locked at a desired position.

In some of the embodiments discloses herein, cannula 140/1140 and or 1145 may also comprise a lock locking the cannula in insertion tunnel 138 and preventing axial movement of the cannula along tunnel 138.

Figure 14A:
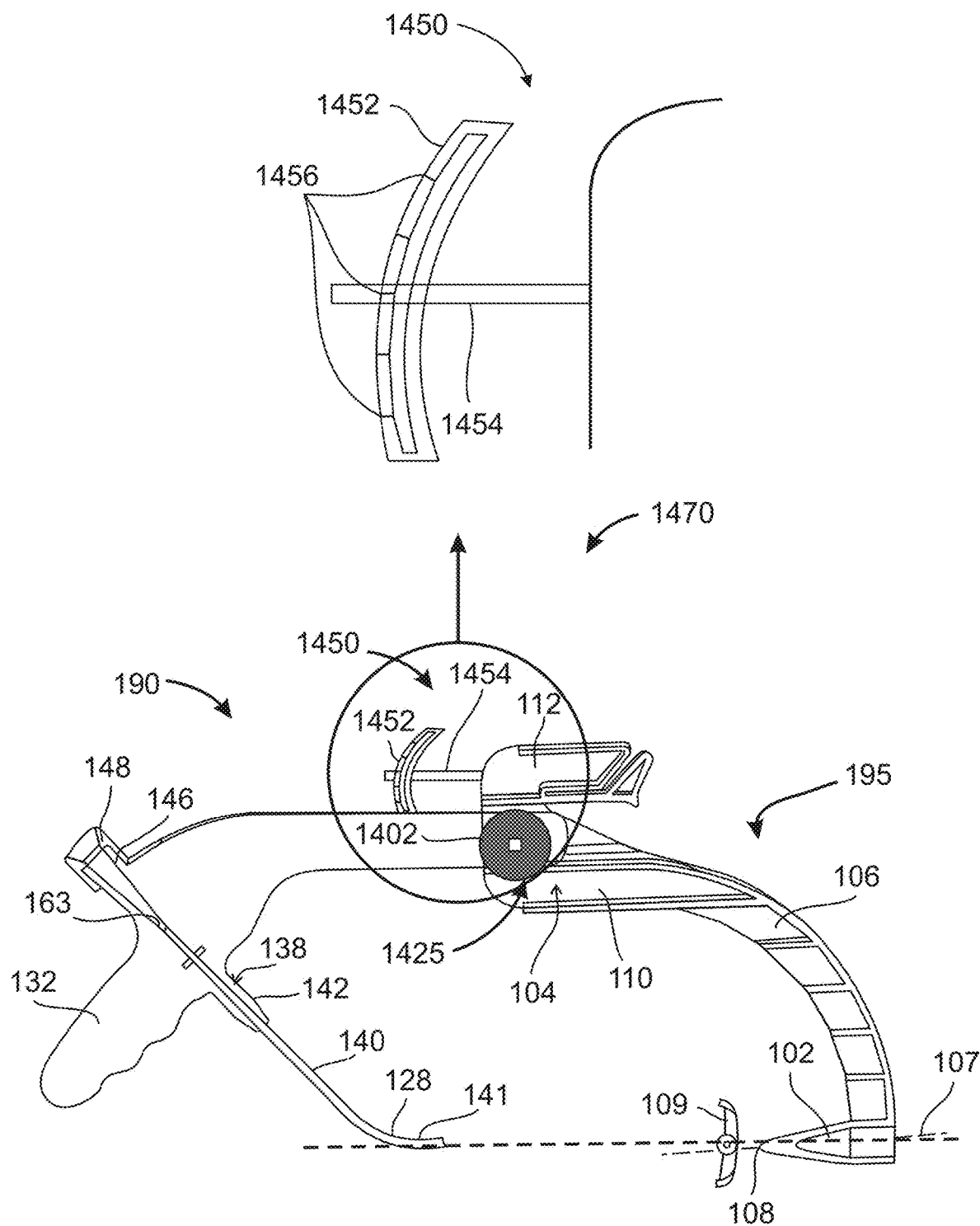
FIGS. 14A, 14B and 14C are side view simplified illustrations of a drill guiding device in accordance with some embodiments of the present invention.
Figure 14B:
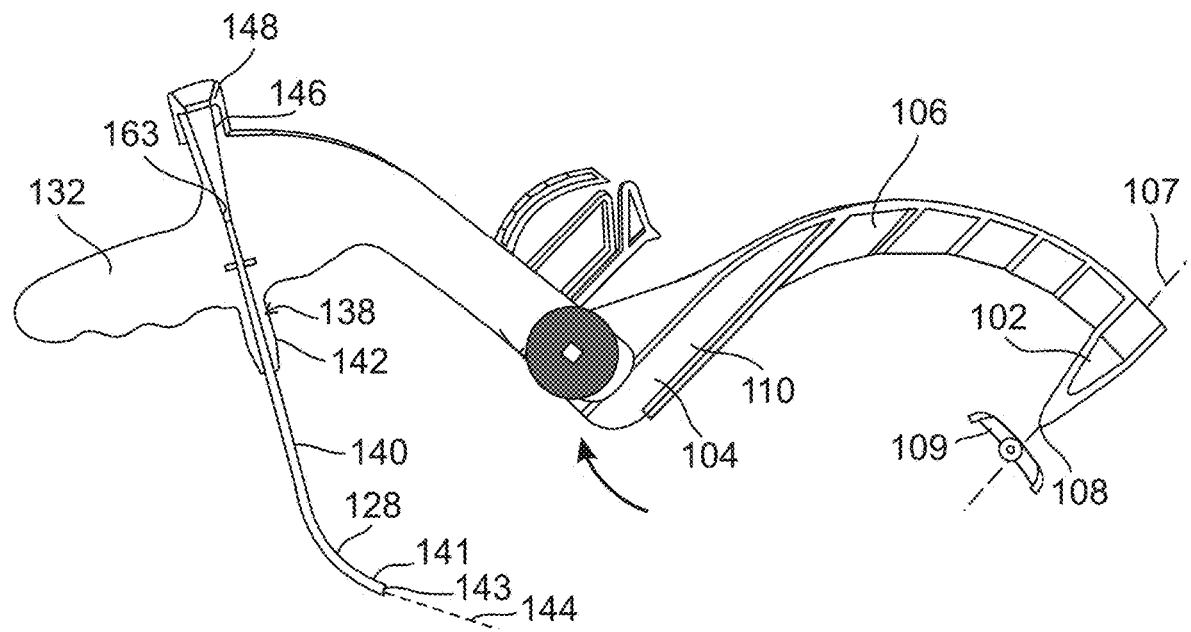
Figure 14C:
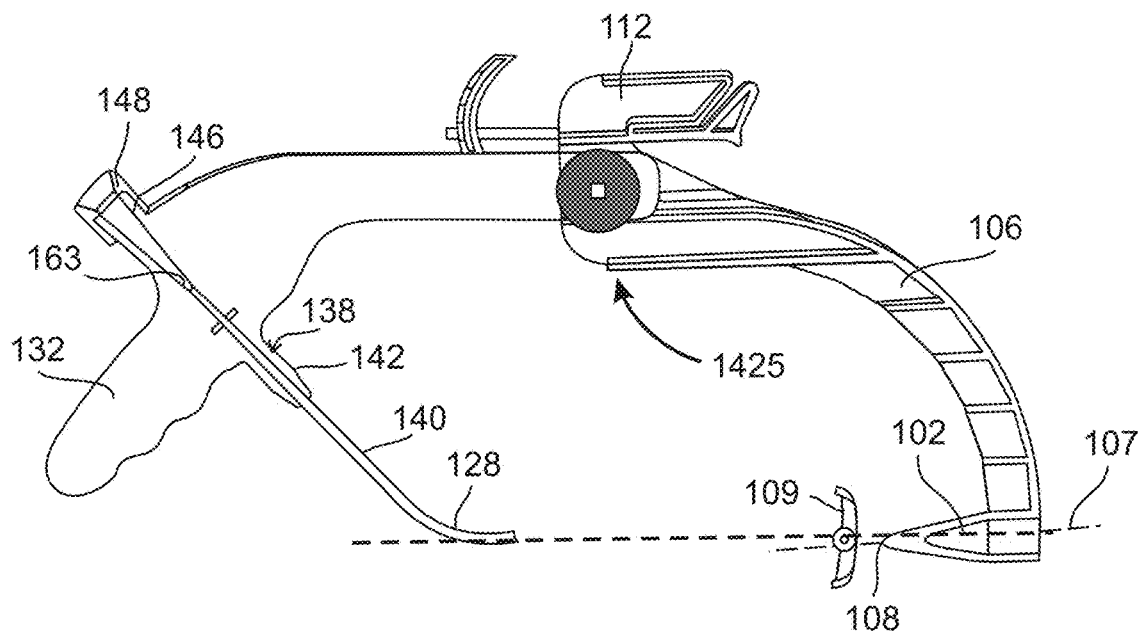

Reference is now made to FIGS. 14A, 14B and 14C, which are side view simplified illustrations of a drill guide device in accordance with some embodiments of the invention. As shown in the exemplary embodiment depicted in FIG. 14A, a drill guide device 1470 comprises a frame comprising at least two parts including a drill entrance side part 190 and a drill exit side part 195 coupled via a rotatable coupling 1425. In some embodiments, rotatable coupling 1425 comprises a locking screw wheel 1402 that tightens and locks drill entrance side part 190 and a drill exit side part 195 to each other at a desired angle. In some embodiments, device 1470 comprises an indicator 1450 that indicates to a user the angular relationship between the longitudinal axis of fixation tip portion 102 and the longitudinal axis of straight distal end 141 of cannula 140. In some embodiments, a first portion 1452 of indicator 1450 is attached to drill entrance side part 190 and a second portion 1454 of indicator 1450 is attached to drill exit side part 195. In some embodiments, first portion 1452 is arcuate and includes markings 1456 that specify the relative angle between longitudinal axes of fixation tip portion 102 and of straight distal end 141 of cannula 140. In some embodiments, second portion 1454 comprises a pointer that rotates circumferentially along arcuate first portion 1452 when drill entrance side part 190 and a drill exit side part 195 are rotatingly adjusted relative to each other.

As shown in the exemplary embodiment in FIGS. 14B, and 14C, drill entrance side part 190 and a drill exit side part 195 are rotated outwardly about rotatable coupling 1425 to be placed into position. In FIGS. 14C, and 14C, drill entrance side part 190 and a drill exit side part 195 are coupled and locked via rotatable coupling 1425 and indicator 1450 indicating that fixation tip portion 102 and the longitudinal axis of straight distal end 141 of cannula 140 are aligned along mutual longitudinal axis 144.

Figure 15A:
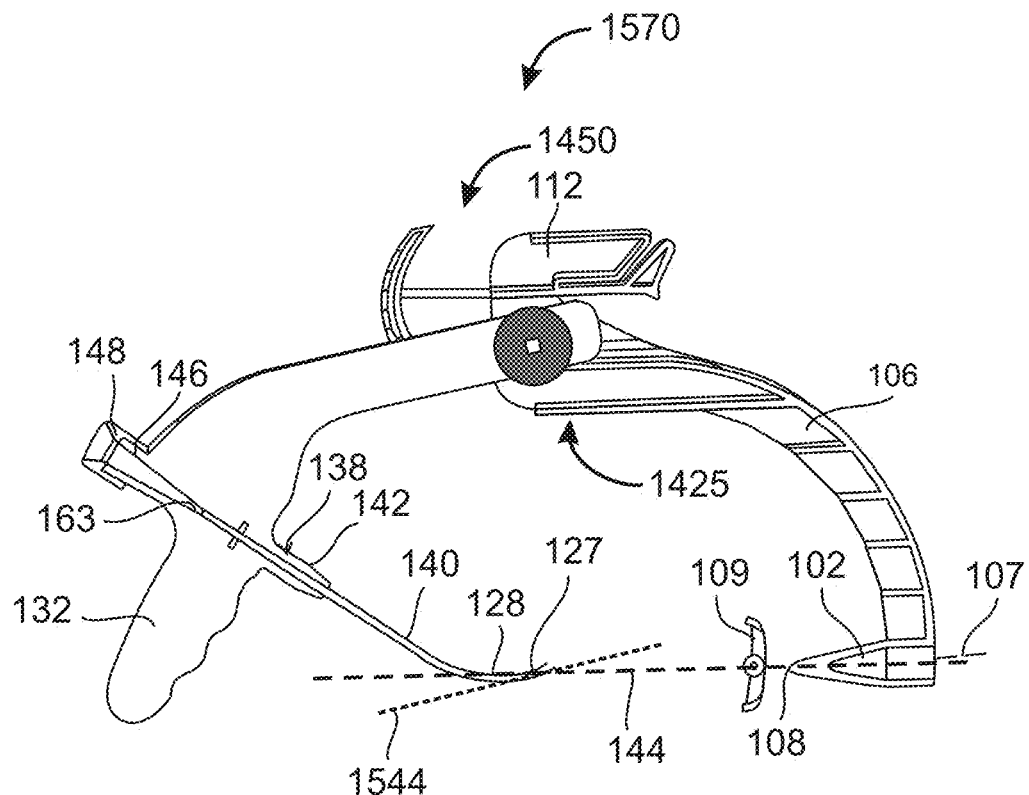
FIGS. 15A and 15B are side view simplified illustrations of a drill guiding device in accordance with some embodiments of the present invention.
Figure 15B:
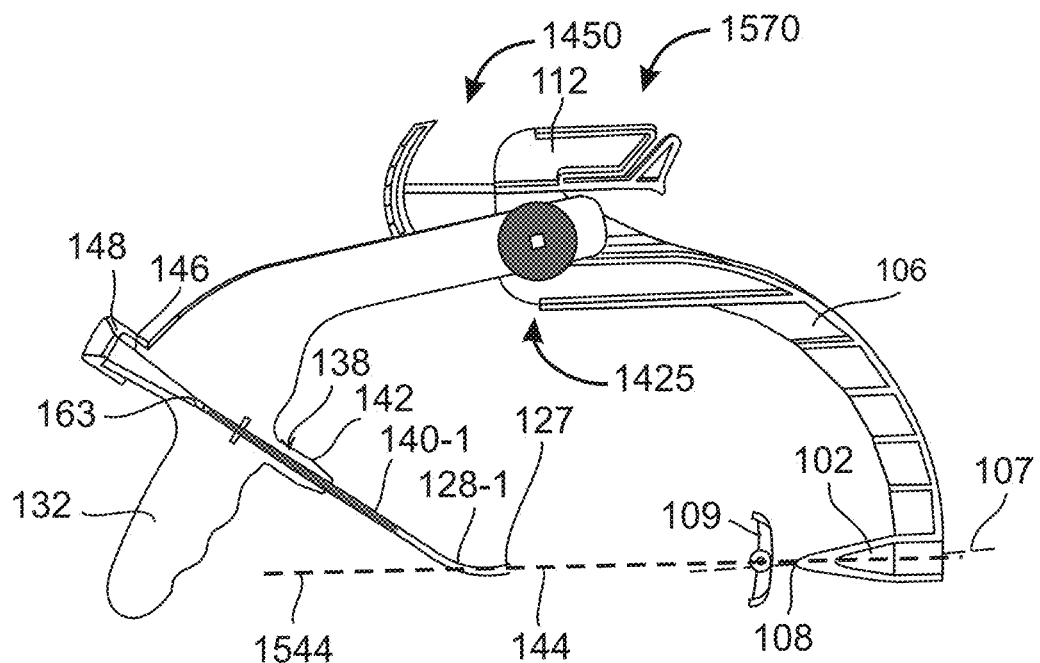

FIGS. 15A and 15B, which are side view simplified illustrations of a drill guide device in accordance with some embodiments of the invention show a device 1570 similar to the device shown in FIGS. 14A-14C. As shown in FIG. 15A, Once placed in position, cannula tip 127 against bone and securing element 109 against skin over an expected exit point of the drill out of the bone, indicator 1450 indicates that the longitudinal axis of fixation tip portion 102 and the longitudinal axis 1544 of straight distal end 141 of cannula 140 are not aligned along mutual longitudinal axis 144. In some embodiments, indicator 1450 indicates an angle (y) between axes 144 and 1544 and or indicate a cannula with a portion 128-1 having the correct angle of bend (shallower, more obtuse or more acute angle) to align fixation tip portion 102 and the straight distal end 141 of cannula 140 along mutual longitudinal axis 144.

As shown in the exemplary embodiment in FIGS. 14B, and 14C, drill entrance side part 190 and a drill exit side part 195 are rotated outwardly about rotatable coupling 1425 to be placed into position. In FIG. 14C, drill entrance side part 190 and a drill exit side part 195 are coupled and locked via rotatable coupling 1425 and indicator 1450 indicating that fixation tip portion 102 and the longitudinal axis of straight distal end 141 of cannula 140 are aligned along mutual longitudinal axis 144.

Figure 16:
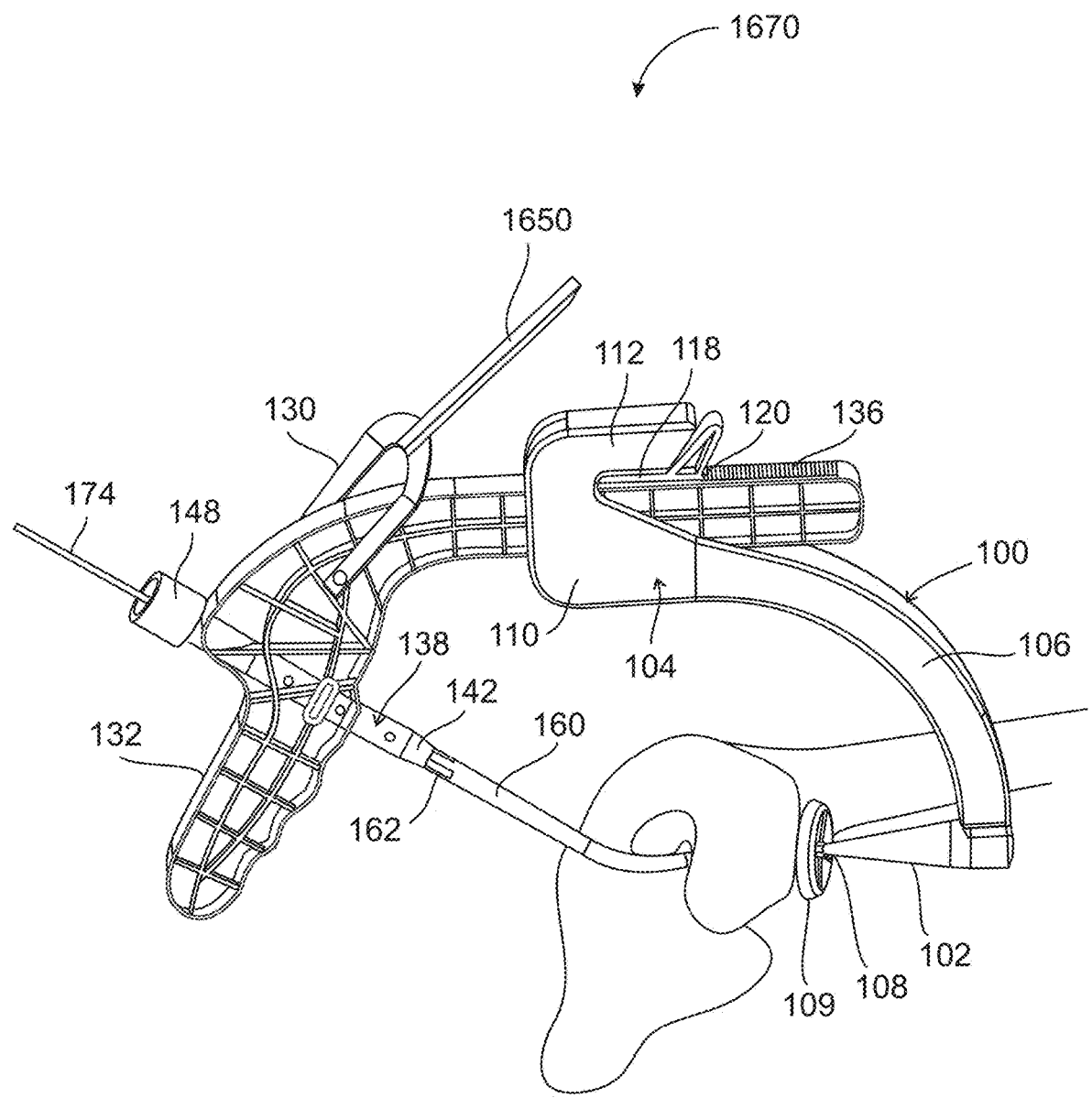
FIG. 16 is a side view simplified illustration of a drill guiding device in accordance with some embodiments of the present invention.

FIG. 16, which is a side view simplified illustration of a drill guide device 1670 in accordance with some embodiments of the invention comprises an indicator arm 1650, that comprises a pointer rotatable about a hinge along a plane defined by drill entrance side part 190 and a drill exit side part 195. Indicator 1650 indicates changes in drilling angle in respect to the plane defined by drill entrance side part 190 and a drill exit side part 195.

It is further appreciated that the guiding device 170 in accordance with an embodiment of the present invention can be utilized for left knee joint in the same manner as for the right knee joint, guiding device 170 obviates the requirement of having two different devices for the left and the right knee joints.

It will be appreciated by persons skilled in the art that the present invention is not limited by what has been particularly shown and described hereinabove. Rather the scope of the present invention includes both combinations and subcombinations of various features described hereinabove as well as variations and modifications thereof which are not in the prior art.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A multiple angle bone drill guiding device, comprising:
    a drill entry part comprising two or more drill insertion tunnels each sized and fitted to receive a cannula;
    at least one cannula each having a distal end portion having a longitudinal axis and a cannula tip and sized to receive a bone drill, at least one of said at least one cannula being a curved cannula;
    a drill exit part comprising a fixation tip portion comprising a fixation tip having a longitudinal axis;
    wherein said longitudinal axis of each said distal end portion of said at least one cannula and said longitudinal axis of said fixation tip portion are arranged on a single mutual axis extending from said cannula tip to said fixation tip; and
    a coupling that rigidly couples said drill entry part and said drill exit part so that said longitudinal axis of said cannula distal end portion of each said at least one curved cannula and said longitudinal axis of said fixation tip portion are arranged along a single mutual axis extending between said cannula tip and said fixation tip,
    wherein said coupling comprises an opening on a first one of said drill entry part and said drill exit part, said opening sized and fitted to slidingly receive a portion of a second one of said drill entry part and said drill exit part.

2. The multiple angle bone drill guiding device according to claim 1, including a coupling that selectively rigidly couples said drill entry part and said drill exit part relative to each other so that said longitudinal axis of said cannula distal end portion of each said at least one curved cannula and said longitudinal axis of said fixation tip portion intersect.

3. The multiple angle bone drill guiding device according to claim 2, wherein said coupling includes a ratchet-type coupling.

4. The multiple angle bone drill guiding device according to claim 1 wherein said portion of the second one of said drill entry part and said drill exit part is configured to slide within said opening along an axis parallel to said single mutual axis.

5. The multiple angle bone drill guiding device according to claim 1, wherein said drill insertion tunnels are arranged in said drill entry part at varying angles ($\beta_1, \beta_2 \ldots \beta_n$) in respect to said single mutual axis; and wherein each of said angles ($\beta$) is defined by a single cannula having a curved portion curved at a corresponding angle ($\Phi$).

6. The multiple angle bone drill guiding device according to claim 1, wherein a drill insertion tunnel selected to be used depends on an angle ($\Phi$) of a curvature of a curved portion of a cannula to be used.

7. The multiple angle bone drill guiding device according to claim 1, wherein said distal end portion of each said at least one cannula is configured to be placed on a surface of a bone and said fixation tip portion is configured to be placed on skin.

8. The multiple angle bone drill guiding device according to claim 1, wherein each of said two or more drill insertion tunnels is configured to accommodate one of said at least one cannula at a respective angle relative to said single mutual axis.

9. The multiple angle bone drill guiding device according to claim 1, wherein said at least one cannula includes a first cannula having a longitudinal axis that lies along said single mutual axis.

10. The multiple angle bone drill guiding device according to claim 1, wherein said fixation tip portion comprises at least one marker that marks an expected drill exit point, wherein said at least one marker has a ring geometry which is coaxial with said single mutual axis.

11. The multiple angle bone drill guiding device according to claim 10, wherein said ring geometry defines a perimeter within which the drill is expected to exit.

12. The multiple angle bone drill guiding device according to claim 11 wherein a diameter of said ring geometry depends on a bending tolerance of the drill.

13. The multiple angle bone drill guiding device according to claim 10 wherein a said marker comprises a sharp end adapted for positioning at a patient's bone.

14. The multiple angle bone drill guiding device according to claim 1, wherein said multiple angle drill guiding device comprises an indicator that indicates the spatial relationship between said longitudinal axis of said cannula distal end portion and said longitudinal axis of said fixation tip portion.

15. The multiple angle bone drill guiding device according to claim 14, wherein a portion of at least one of the drill entry part and the drill exit part comprises said indicator.

16. The multiple angle bone drill guiding device according to claim 14, wherein said drill entry part comprises a linear connecting portion including said indicator.

17. The multiple angle bone drill guiding device according to claim 1, wherein said opening is on said drill exit part, said opening sized and fitted to slidingly receive the portion of the drill entry part.

18. The multiple angle bone drill guiding device according to claim 1, wherein said coupling includes:
    a plurality of stations on said second one of said drill entry part and said drill exit part; and
    a stopper on said first one of said drill entry part and said drill exit part, wherein said stopper is slidable relative to said stations, to a selected one of a plurality of lockable positions and wherein at said selected lockable position said stopper is rotatable to lock said drill entry part and said drill exit part in said desired lockable position relative to each other.

19. The multiple angle bone drill guiding device according to claim 1, wherein said coupling includes a ratchet-type coupling.

20. A multiple angle bone drill guiding device, comprising:
    a drill entry part comprising two or more drill insertion tunnels each sized and fitted to receive a cannula;
    at least one cannula each having a distal end portion having a longitudinal axis and a cannula tip and sized to receive a bone drill, at least one of said at least one cannula being a curved cannula;
    a drill exit part comprising a fixation tip portion comprising a fixation tip having a longitudinal axis;
    wherein said longitudinal axis of each said distal end portion of said at least one cannula intersects with said longitudinal axis of said fixation tip portion.

* * * * *